(12) United States Patent
Breuninger et al.

(10) Patent No.: US 9,480,257 B2
(45) Date of Patent: Nov. 1, 2016

(54) CAPSULE SUSPENSION FORMULATIONS OF DITHIOPYR HERBICIDE

(71) Applicant: DOW AGROSCIENCES LLC, Indianapolis, IN (US)

(72) Inventors: James M. Breuninger, Zionsville, IN (US); Ronald L. Cassell, New Palestine, IN (US); James M. Gifford, Lebanon, IN (US); Daniel L. Loughner, Lawrenceville, NJ (US); Michael W. Melichar, Zionsville, IN (US); David G. Ouse, Indianapolis, IN (US); Michelle S. Smith, Carmel, IN (US); Mike P. Tolley, Indianapolis, IN (US); Stephen L. Wilson, Zionsville, IN (US); Dennis G. Wujek, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/203,109

(22) Filed: Mar. 10, 2014

(65) Prior Publication Data
US 2014/0274716 A1 Sep. 18, 2014

Related U.S. Application Data

(60) Provisional application No. 61/785,066, filed on Mar. 14, 2013.

(51) Int. Cl.
*A01N 25/28* (2006.01)
*A01N 43/40* (2006.01)

(52) U.S. Cl.
CPC .................................... *A01N 43/40* (2013.01)

(58) Field of Classification Search
None
See application file for complete search history.

(56) References Cited

U.S. PATENT DOCUMENTS

| | | | |
|---|---|---|---|
| 4,563,212 A | 1/1986 | Becher et al. | |
| 5,686,385 A | 11/1997 | Akashi et al. | |
| 5,925,464 A | 7/1999 | Mulqueen et al. | |
| 5,972,363 A * | 10/1999 | Clikeman et al. | 424/408 |
| 7,754,655 B2 | 7/2010 | Wolf et al. | |
| 2011/0301036 A1* | 12/2011 | Tank et al. | 504/347 |
| 2012/0329649 A1 | 12/2012 | Hunter et al. | |

FOREIGN PATENT DOCUMENTS

| | | | |
|---|---|---|---|
| JP | 2000143407 | * | 5/2000 |
| WO | 0047044 A1 | | 8/2000 |
| WO | 2012024524 A1 | | 2/2012 |

OTHER PUBLICATIONS

International Search Report and Written Opinion for PCT/US2014/022732 dated Aug. 1, 2014.

* cited by examiner

*Primary Examiner* — Alton Pryor
(74) *Attorney, Agent, or Firm* — Michael R. Asam; Magleby Cataxinos & Greenwood

(57) ABSTRACT

Dithiopyr capsule suspension formulations, possessing a broad range of capsule wall thicknesses and diameters are disclosed. These capsules have decreased volatility and provide enhanced biological activity when compared with commercial dithiopyr in water formulations.

30 Claims, 19 Drawing Sheets

CAPSULE SUSPENSION FORMULATIONS OF DITHIOPYR HERBICIDE

CROSS-REFERENCE TO RELATED APPLICATION

This application claims the benefit of U.S. Provisional Patent Application Ser. No. 61/785,066, filed Mar. 14, 2013, the disclosure of which is hereby incorporated herein in its entirety by this reference.

BACKGROUND

Controlling unwanted plants is essential to modern agriculture. Currently, safe and effective herbicide formulations play a significant role in controlling weed populations. Properties of useful herbicide formulations include good efficacy against targeted plants, including good initial toxicity against targeted plants, ease of handling, stability, advantageous residence times in the environment and, in some instances, a long effective period of herbicidal activity after its application to an area.

BRIEF SUMMARY

Embodiments include compositions comprising capsules containing dithiopyr. In some embodiments, the capsules may range from 1 micrometer to 10 micrometers in diameter, about 1 micrometer to about 10 micrometers in diameter, or may be 1, 2, 3, 4, 5, 6, 7, 8, 9, or 10, or more micrometers in diameter. In embodiments, a composition may contain capsules having different diameters.

In certain embodiments, the capsules may have a wall thickness ranging from 10 nanometers to 100 nanometers, about 10 nanometers to about 100 nanometers, or may have a wall thickness of 10, 15, 20, 25, 30, 35, 40, 45, 50, 55, 60, 65, 70, 75, 80, 85, 90, 95, or 100 nanometers. In embodiments a composition may contain capsules having different wall thicknesses.

Examples of capsules include, but are not limited to, (parameters expressed as X/Y where diameter in micrometers=X, and a wall thickness in nanometers=Y) 2/10, 2/20, 2/30, 2/60, 2/100, 6/10, 6/20, 6/30, 6/60, 6/100, 10/10, 10/20, 10/30, 10/40, 10/50, 10/60, and 10/100. In some embodiments, compositions may contain one or more of the different capsules. In other embodiments, a composition may comprise first capsules having a diameter of 10 micrometers and a wall thickness of 10 nanometers, and second capsules having a diameter of 10 micrometers and a wall thickness of 100 nanometers.

In certain embodiments the compositions may be applied to an area to control the growth of an unwanted plant. For example, the unwanted plant may be crabgrass (*Digitaria* sp.), annual bluegrass (*Poa annua*), goosegrass (*Eleusine indica*), broad leaf weeds (e.g., chickweed, henbit, yellow sorrel, spurge, burweed, clover, purslane, lambsquarters, etc.). Additionally, the unwanted plant may be *Digitaria sanguinalis* or *Setaria* spp.

In particular embodiments, the compositions may be applied to an area to achieve a concentration of from about 30 grams active ingredient/hectare to about 500 grams active ingredient/hectare dithiopyr, 30 grams active ingredient/hectare to 500 grams active ingredient/hectare, or 31.3, 62.5, 125, 200, 250, 280, 330, 420, or 500, or more grams active ingredient/hectare dithiopyr. In some embodiments, the compositions may be applied to an area to achieve a concentration of from about 0.03 lbs active ingredient/acre dithiopyr to about 0.5 lbs active ingredient/acre dithiopyr, 0.03 lbs active ingredient/acre dithiopyr to 0.5 lbs active ingredient/acre dithiopyr, or 0.03, 0.06, 0.11, 0.12, 0.22, 0.25, or 0.5, or more lbs active ingredient/acre dithiopyr.

In other embodiments, the compositions may be applied to an area pre-emergent to the plant whose growth is to be controlled, post-emergent to the plant whose growth is to be controlled, or both. A composition according to the invention may be applied one or more times in one year.

DETAILED DESCRIPTION

Figure 1:
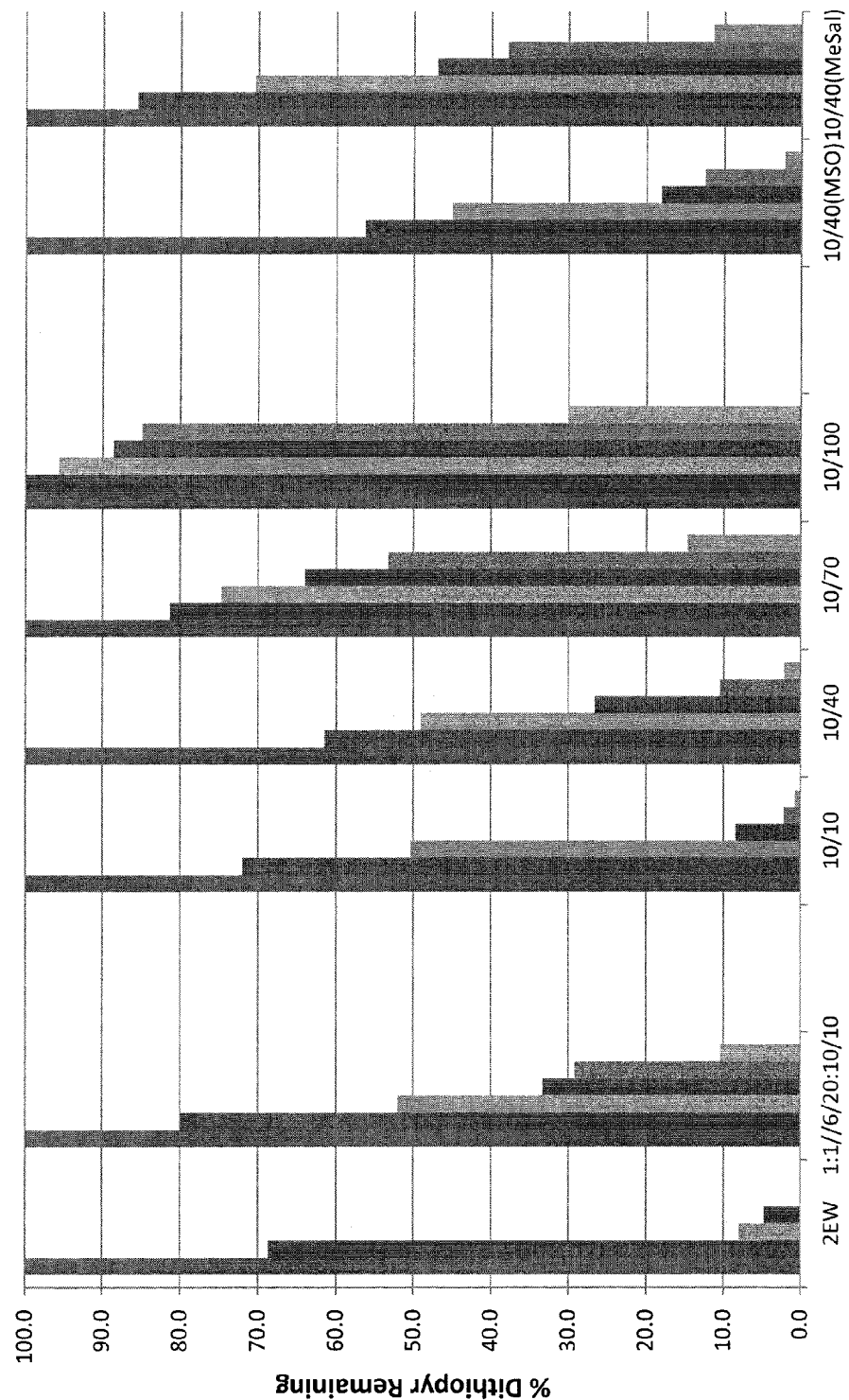
FIG. 1 is a graphical representation of the results of volatility testing of compositions according to a particular embodiment. For each composition tested, the bars proceed from left to right as Days, 0, 3, 7, 14, 28, and 56. MeSal indicates the presence of methyl salicylate in the composition at 40 g/L. MSO indicates the presence of methylated seed oil in the composition at 42 g/L.

Embodiments include compositions comprising capsules containing dithiopyr. In some embodiments, the capsules may range from 1 micrometer to 10 micrometers in diameter, about 1 micrometer to about 10 micrometers in diameter, or may be 1, 2, 3, 4, 5, 6, 7, 8, 9, or 10, or more micrometers in diameter. In other embodiments, a composition may contain capsules having different diameters.

In certain embodiments, the capsules may have a wall thickness ranging from 10 nanometers to 100 nanometers, about 10 nanometers to about 100 nanometers, or may have a wall thickness of 10, 15, 20, 25, 30, 35, 40, 45, 50, 55, 60, 65, 70, 75, 80, 85, 90, 95, or 100, or more nanometers. In other embodiments a composition may contain capsules having different wall thicknesses.

Examples of capsules include, but are not limited to, (parameters expressed as X/Y where diameter in micrometers=X, and a wall thickness in nanometers=Y) 2/10, 2/20, 2/30, 2/60, 2/100, 6/10, 6/20, 6/30, 6/60, 6/100, 10/10, 10/20, 10/30, 10/60, and 10/100. In particular embodiments, compositions may contain one or more of the different capsules. In other embodiments, a composition may comprise first capsules having a diameter of 10 micrometers and a wall thickness of 10 nanometers and second capsules having a diameter of 10 micrometers and a wall thickness of 100 nanometers.

In certain embodiments, dithiopyr may be contained/encapsulated in the capsules. As used herein, the terms "encapsulate," "encapsulated" and "encapsulation" mean and include to surround, encase, or protect in a capsule.

As used herein, the term "microcapsule" means and includes a particle(s) of the dithiopyr encapsulated within a polymeric material, such as polyurea.

As used herein, the terms "shell" and "wall" mean and include an assembly of a polymeric material, such as polyurea, disposed on or encapsulating a surface of a core including dithiopyr. Such terms do not necessarily imply that a given shell or wall is completely uniform or that it completely encompasses whichever materials or components that are localized within the corresponding microcapsule.

Embodiments of herbicidal formulations including dithiopyr may be at least partially encapsulated within a polyurea shell (i.e., a microcapsule). The herbicide within the shell may be present as a stable organic capsule suspension of a substituted pyridine carbodithioate herbicide (e.g., dithiopyr). The herbicidal formulations provide effective pest control with improved chemical and physical stability. Such improved stability may be obtained by using a cross-linking amine and an isocyanate monomer to form the microcapsule polyurea shell. Methods of forming the herbicidal formulations and methods of controlling weeds (e.g., crab grass or broadleaf weeds) using the herbicidal formulations are also disclosed.

The shell that at least partially encases the dithiopyr may be formed by a reaction (e.g., an interfacial polycondensation reaction) between at least one monomer that is essentially insoluble in water (i.e., a hydrophobic monomer) and at least one monomer that is soluble in water (i.e., a hydrophilic monomer). Examples of hydrophobic monomers that may be used to form the shell of the microcapsule include, but are not limited to, isocyanates, diisocyanates, polyisocyanates, diacid chlorides, poly acid chlorides, sulfonyl chlorides and chloroformates. The term "isocyanate" as used herein may include isocyanates, diisocyanates, polyisocyanates and mixtures thereof. As a non-limiting example, the hydrophobic monomer may be an isocyanate such as PAPI® 27 polymethylene polyphenylisocyanate, which is marketed by Dow Chemical Company (Midland, Mich.).

Examples of cross-linking agents that may be used to form the shell of the microcapsule include, but are not limited to, cross-linking amines such as diamines and polyamines, water-soluble diols and water-soluble polyols (e.g., polyvinyl alcohol), and combinations thereof. The capsule forming reaction may be carried out in the presence of a cross-linking amine. For example, a polyurea shell may be formed by reacting a hydrophobic isocyanate monomer and the cross-linking amine. Examples of cross-linking amines that may be used to form the shell of the microcapsule include, but are not limited to, ethylenediamine (EDA), diethylenetriamine (DETA), tetramethylenediamine, N,N',-dimethyl piperazine, N-ethylpiperazine 1,2-cyclohexyldiamine, triethylenetetramine and piperazine.

The dithiopyr formulations may be prepared, for example, using an emulsion polymerization process that comprises combining an aqueous phase that includes the hydrophilic monomer (e.g., the cross-linking amine) into an organic phase that includes the hydrophobic monomer (e.g., the isocyanate) and the herbicide. The hydrophobic monomer and the hydrophilic monomer are reacted to form a polymeric shell around a core of the dithiopyr dispersed within an organic phase. The herbicide formulations may be prepared by a batch process, an in-line or continuous process, or a combination of the two. Such processes may be designed and optimized to the desired output parameters and operated by one of ordinary skill in the art.

The organic or oil phase may be formed by combining dithiopyr in a solvent. The solvent may be a hydrocarbon fluid, such as Aromatic 150 ND or SOLVESSO® 150 ND that are commercially available from Exxon Mobile Chemical Company (Houston, Tex.). In some embodiments, the solution of the dithiopyr in the solvent may be formed to furnish about 11 wt %, about 11.6 wt %, about 11.8 wt %, or about 12 wt % or more dithiopyr in the finished capsule suspension. In other embodiments, the dithiopyr may comprise about 11.6% or 11.8% of the finished capsule suspension by weight. In some embodiments, the solution of the dithiopyr in the solvent may be formed to include 1 to 70 wt % or dithiopyr in the solvent. In embodiments, the dithiopyr may comprise at least 1%, at least 2%, at least 3%, at least 4%, least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20% by weight of the finished capsule suspension.

In some embodiments, the solution of dithiopyr in the solvent may comprise 30% to 50% of the total weight of the dithiopyr/solvent solution. In certain embodiments, dithiopyr may comprise about 33 wt %, about 34.1 wt %, or about 35 wt % of the dithiopyr/solvent solution. In other embodiments, the dithiopyr may comprise at least 1%, at least 5%, at least 10%, at least 15%, at least 20%, least 25%, at least 30%, at least 31%, at least 32%, at least 33%, at least 34%, at least 35%, at least 36%, at least 37%, at least 38%, at least 39%, at least 40%, at least 45%, at least 50%, at least 60%, or at least 70% by weight of the dithiopyr/solvent solution.

In embodiments, the organic phase may additionally contain one or more herbicides or pesticides in addition to dithiopyr and/or oil soluble adjuvants, thinners, thickeners, diluents, surfactants or rheological aids. In certain embodiments, the organic phase may contain methyl salicylate and/or methylated seed oil. In some embodiments, the methyl salicylate and/or methylated seed oil may be present in the dithiopyr/solvent solution at a ratio from about 1:1 to 25:1 dithiopyr:methyl salicylate and/or methylated seed oil. In other embodiments, the ratio of dithiopyr to methyl salicylate and/or methylated seed oil may be 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1. In a particular embodiment, the dithiopyr may be present at 120 g/L and methyl salicylate at 40 g/L. In embodiments, the herbicide or pesticide in addition to dithiopyr may be an oil soluble herbicide. By way of example, and without limitation, the oil-soluble herbicide in addition to dithiopyr may be one or more of acetochlor, alachlor, ametryn, amidosulfuron, anilofos, atrazine, azafenidin, azimsulfuron, benfluralin, benfuresate, bensulfuron-methyl, bensulide, benzfendizone, benzofenap, bromobutide, bromofenoxim, butachlor, butafenacil, butamifos, butralin, butylate, cafenstrole, carbetamide, chlorbromuron, chloridazon, chlorimuron-ethyl, chlorotoluron, chlorpropham, chlorsulfuron, chlorthal-dimethyl, chlorthiamid, cinidon-ethyl, cinmethylin, cinosulfuron, clomazone, clomeprop, cloransulam-methyl, cyanazine, cycloate, cyclosulfamuron, daimuron, desmedipham, desmetryn, dichlobenil, diflufenican, dimefuron, dimepiperate, dimethachlor, dimethametryn, dimethenamid, dinitramine, dinoterb, diphenamid, diuron, EPTC, esprocarb, ethalfiuralin, ethametsulifuron-methyl, ethofumesate, ethoxysulfuron, etobenzanid, ferioxaprop-ethyl, fenuron, flamprop-methyl, flazasulfuron, fluazolate, fluchloralin, flumetsulam, flumiclorac-pentyl, flumioxazin, fluometuron, fluorochloridone, flupoxam, flurenol, fluridone, fluoroxypyr-1-methylheptyl, flurtamone, fluthiacet-methyl, halosulfuron, hexazinone, imazosulfuron, indanof an, isoproturon, isouron, isoxaben, isoxaiflutole, lenacil, linuron, mefenacet, metamitron, metazachior, methabenzthiazuron, methyldymron, metobenzuron, metobromuron, metolachlor, metosulam, metoxuron, metribuzin, metsulifuron, molinate, monolinuron, naproanilide, napropamide, neburon, nicosulfuron, norfiurazon, orbencarb, oryzalin, oxadiargyl, oxadiazon, oxasulfuron, pebulate, pendimethalin, pentanochlor, pentoxazone, phenmedipham, piperophos, pretilachlor, primisulfuron, prodiamine, profluazol, prometon, prometryn, propachlor, propanhl, propazine, propham, propisochlor, propyzamide, prosulfocarb, prosulfuron, pyraflufen-ethyl, pyrazogyl, pyrazolynate, pyrazosulfuron-ethyl, pyrazoxyfen, pyributicarb, pyridate, pyriminobac-methyl, quinclorac, quinmerac, rimsulfuron, siduron, simazine, simetryn, sulcotrione, sulfentrazone, sulfometuron, sulfosulfuron, tebutam, tebuthiuron, terbacil, terbumeton, terbuthylazine, terbutryn, thenyichlor, thiazopyr, thidiazimin, thifensulfuron, thiobencarb, tiocarbazil, triallate, triasulfuron, tribenuron, trietazine, trifluralin, triflusulfuron and vernolate.

The aqueous phase and the organic phase may be combined to form a mixture that includes two immiscible phases (i.e., a dual-phase mixture). The dual-phase mixture may be subjected to a conventional high shear emulsification process to disperse the oil phase into the aqueous phase. As the oil phase is dispersed in the aqueous phase, a plurality of particles of the oil phase may form within the aqueous phase. The emulsification process may be continued until a desired particle size (i.e., the volume mean diameter of the particles) is achieved. Thus, the particle size may be controlled by adjusting at least one of a length of time or a speed at which the mixture is subjected to emulsification. For example, the particle size may be between about 1 micron (μm) and about 30 μm and, more particularly, between about 1 μm and about 10 μm.

A cross-linking amine, such as the EDA, may then be added to the emulsion and may react with isocyanate groups of the hydrophobic monomer, such as the PAPI® 27 polymethylene polyphenylisocyanate, at an interface between the oil phase particles and the aqueous phase to form the microcapsule polyurea shell. After addition of the cross-linking amine, the mixture may be maintained at a temperature of between about 20° C. and about 60° C. and, more particularly, between about 20° C. and about 30° C.

The resulting herbicidal capsule formulation is a microcapsule suspension that includes the oil phase liquid particles at least partially encapsulated by the shell and suspended in the aqueous phase. The oil phase particles may be referred to herein as the "core" of the microcapsules. In embodiments in which the hydrophobic monomer comprises an isocyanate and the cross-linking amine comprises EDA, the shell of the microcapsules may comprise a polyurea. By adjusting the length of time during which the mixture is subjected to emulsification and/or a speed of mixing, a thickness of the polyurea shell may be varied. Similarly, the amounts of isocyanate, cross-linking amines, and other ingredients may be adjusted to form capsules with varying sizes and shell thicknesses.

The processing method used to prepare the dithiopyr formulations may be a combination of a batch process and a continuous, in-line emulsification process. The organic and aqueous phases may be prepared as described herein and may then be individually metered into an inline rotor/stator homogenizer, or similar device, at an aqueous to oil volume ratio of about 0.75 to about 1.10. The size of the emulsion oil droplet formed may be controlled by the feed rates into the homogenizer and the rotational speed of the homogenizer. For example, the particle size may be between about 1 μm and about 30 μm and, more particularly, between about 1 μm and about 10 μm. The cross-linking amine solution may then be added in-line to the out-flow of the emulsion from the homogenizer using another metering system to add the second component for the polyurea shell formation. The resulting stream may then be collected into a finishing vessel where any finishing agents, as described herein, may be added to complete the formulation. The PAPI® 27 isocyanate may alternatively be added as a separate stream to the homogenizer by adding another metering system. The processing described herein may be designed, optimized and operated by one of ordinary skill in the art.

The calculation of the amounts of capsule wall components needed to achieve a target wall thickness was based on the geometric formula relating the volume of a sphere to its radius. If a core-shell morphology is assumed, with the core comprised of the non wall-forming, water-insoluble components (i.e., the dithiopyr and the solvent) and the shell made up of the polymerizable materials (i.e., the isocyanate and the amine), then equation (1) holds, relating the ratio of the volume of the core ($V_c$) and the volume of the core, plus the volume of the shell ($V_s$) to their respective radii, where $r_s$ is radius of the capsule including the shell and $I_s$ $l_s$ is thickness of the shell.

$$\frac{V_C + V_S}{V_C} = \left(\frac{r_S}{r_S - l_S}\right)^3 \quad (1)$$

Solving equation (1) for the volume of the shell yields:

$$V_S = V_C\left(\left(\frac{r_S}{r_S - l_S}\right)^3 - 1\right) \quad (2)$$

Substituting masses ($m_i$) and densities ($d_i$) for their respective volumes ($m_s/d_s = V_s$ and $m_c/d_c = V_c$, where the subscript s or c refers to the shell or core, respectively) and solving for the mass of the shell gives:

$$m_S = m_C \frac{d_S}{d_C}\left(\left(\frac{r_S}{r_S - l_S}\right)^3 - 1\right) \quad (3)$$

In order to simplify the calculation and directly use the respective weights of the core and shell components, the approximation that the density ratio $d_s/d_c$ is approximately equal to one was made yielding equation (4).

$$m_S \approx m_C\left(\left(\frac{r_S}{r_S - l_S}\right)^3 - 1\right) \quad (4)$$

Making the substitutions $m_C = m_O - m_{OSM}$, $m_S = m_O + (f_{WSM/OSM}))m_{OSM} - m_C$, and $f_{WSM/OSM} = m_{WSM}/m_{OSM}$ (a ratio of hydrophilic monomer to hydrophobic monomer), where $m_O$ is a total mass of the oil components (e.g., the dithiopyr, the solvent and the hydrophobic monomer), $m_{OSM}$ is the mass of the hydrophobic monomer, and $m_{WSM}$ is the mass of the hydrophilic monomer, and solving for $m_{OSM}$ yields:

$$m_{OSM} = \frac{m_o\left(\left(\frac{r_S}{r_S - l_S}\right)^3 - 1\right)}{f_{WSM/OSM} + \left(\frac{r_S}{r_S - l_S}\right)^3} \quad (5)$$

For the determination of $m_{OSM}$, the entire quantity of $m_{WSM}$ was used in the calculation The herbicidal formulations may be formed such that the shell of each microcapsule has an average thickness of between about 2 nanometers (nm) to about 100 nm and, more particularly, between about 2 nm to about 50 nm. For example, an average thickness of the shells may be about 40 nm.

One or more finishing agents may be added to the herbicidal capsule formulation. Such finishing agents include, for example, one or more surfactants, thickeners, preservatives, antifoaming agents and buffers. Examples of suitable surfactants include, but are not limited to, a graft copolymer of alkylphenolethoxylate and polyalkyleneglycoletheracryl, such as that commercially available from Croda Chemicals Ltd. (England) under the trade name ATLOX™ 4913 polymeric surfactant, GEROPON® sodium dioctyl sulfosuccinate (SDS), which is commercially available from Rhodia Novecare (Canbury, N.J.), and GOHSENOL™ GL03 polyvinyl alcohol. Suitable thickeners include, but are not limited to, xanthan gum (e.g., KELZAN® xanthan gum, which may be obtained commercially from CP Kelco U.S., Inc., Atlanta, Ga.), a microcrystalline cellulose gel, such as AVICEL® CL 611, which is commercially available from FMC Corporation (Philadelphia, Pa.) and silicates (e.g., VEEGUM® magnesium aluminum silicate, which may be obtained commercially from R.T. Vanderbilt Company, Inc., Norwalk, Conn.). An example of a suitable preservative includes, but is not limited to, PROXEL® GXL preservative (Arch UK Biocides Limited, England). For example, GOHSENOL™ GL03 polyvinyl alcohol, VEEGUM® magnesium aluminum silicate, KELZAN® ASX xanthan gum, and PROXEL® GXL preservative may optionally be added to the aqueous phase after formation of the herbicidal capsule suspension. An example of suitable antifoaming agents includes, but is not limited to, silicone-based anti-foaming agents. Such a silicon-based antifoaming agent is available from Harcros Chemicals, Inc. (Kansas City, Kans.) under the trade name Antifoam 100 IND. The buffer may include, for example, an aqueous solution of a weak acid and its conjugate base or a weak base and its conjugate acid. The buffer solution may be formulated to maintain a desired pH of the dithiopyr formulation.

In one embodiment of the invention, a composition comprising capsules containing dithiopyr may have the following components:

| COMPONENT | WT % |
|---|---|
| Dithiopyr | 11.66 |
| SOLVESSO ® 150 ND | 22.79 |
| PAPI ® 27 Isocyanate | 0.69 |
| Polyvinyl alcohol | 0.89 |
| Ethylenediamine | 0.17 |
| Water | 62.9 |
| VEEGUM ® | 0.18 |
| KELZAN ® S | 0.02 |
| PROXEL ® GXL | 0.09 |

In embodiments, a composition comprising dithiopyr containing capsules may have from about 30 to about 240 g/L dithiopyr, 120 to 240 g/L dithiopyr, or 30, 40, 50, 60, 70, 80, 90, 100, 110, 120, 130, 140, 150, 160, 170, 180, 190, 200, 210, 220, 230, or 240, or more g/L dithiopyr.

The aqueous herbicidal capsule formulations may be optionally diluted in a carrier such as water and packaged or applied directly to the area where weeds are to be controlled. The herbicidal formulations may be as effective against unwanted plants/weeds as the non-encapsulated formulations, but, in comparison, may exhibit significantly reduced toxicity to crops, ornamental plants, mammals, less environmental impact, and enhanced stability. Furthermore, the herbicidal formulations may maintain their herbicidal properties for a substantially increased time period in comparison to non-encapsulated formulations, especially liquid based formulations.

In other embodiments, the compositions may be applied to an area to control the growth of an unwanted plant. In some embodiments, the unwanted plant may be crabgrass (*Digitaria* sp.), annual bluegrass (*Poa annua*), goosegrass (*Eleusine indica*), or broad leaf weeds (e.g., chickweed, henbit, yellow sorrel, spurge, burweed, clover, purslane, lambsquarters, etc.). Additionally, the unwanted plant may be *Digitaria sanguinalis* or *Setaria* spp.

In alternative embodiments, the compositions may be applied to an area to achieve a concentration of from about 30 grams active ingredient/hectare to about 500 grams active ingredient/hectare dithiopyr, 30 grams active ingredient/hectare to 500 grams active ingredient/hectare, or 31.3, 62.5, 125, 200, 250, 280, 330, 420, or 500, or more grams active ingredient/hectare dithiopyr. In particular embodiments, the compositions may be applied to an area to achieve a concentration of from about 0.03 lbs active ingredient/acre dithiopyr to about 0.5 lbs active ingredient/acre dithiopyr, 0.03 lbs active ingredient/acre dithiopyr to 0.5 lbs active ingredient/acre dithiopyr, or 0.03, 0.06, 0.11, 0.12, 0.22, 0.25, or 0.5, or more lbs active ingredient/acre dithiopyr.

In certain embodiments, the compositions may be applied to an area pre-emergent to the plant whose growth is to be controlled, post-emergent to the plant whose growth is to be controlled, or both. In embodiments, a composition according to the invention may be applied one or more times in one year.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

EXAMPLES

The present invention is further described in the following examples, which are offered by way of illustration and are not intended to limit the invention in any manner.

Example 1

Process for Creating Formulations Containing Diothiopyr in 10/40 Microcapsules

The total composition for this formulation is as follows:

| Component | Wgt % | Wgt (g) |
|---|---|---|
| Dithiopyr | 11.66 | 163.04 |
| Technical Impurities | 0.61 | 8.58 |
| Aromatic 150 Solvent | 22.79 | 317.73 |
| PAPI ® 27 | 0.69 | 9.64 |
| Ethylene Diamine (EDA) | 0.17 | 2.32 |
| Polyvinyl Alcohol (PVA) | 0.89 | 12.50 |
| VEEGUM ® | 0.18 | 2.50 |
| KELZAN ® S | 0.02 | 0.30 |
| PROXEL ® GXL | 0.09 | 1.25 |
| Water | 62.90 | 897.58 |

Preparation of the Organic Phase.

317.73 grams of Aromatic 150 solvent was added to a clean dry vessel. To the solvent, 171.62 grams of Dithiopyr technical was added and stirred with a low shear mixer until the Dithiopyr was dissolved. 9.64 grams of PAPI® 27 was added and stirred with a low shear mixer until thoroughly mixed. If desired, methyl salicylate and/or methylated seed oil may be added to the organic phase.

Preparation the Aqueous Phase

In a clean dry vessel large enough to contain the entire finished batch of product, 483.45 grams of water was added. Added to the water were 2.50 grams of VEEGUM® and 0.30 grams of KELZAN® S. These three components were mixed until the KELZAN® and VEEGUM® were completely hydrated. This was done using a high shear mixer such as a Silverson mixer at low speed to prevent foaming. Once the VEEGUM® and KELZAN® were thoroughly mixed, 12.5 grams of PVA and 1.25 grams of PROXEL® GXL were added. The composition was then thoroughly mixed using the Silverson mixer at low speed.

Formation of the Emulsion

With the Silverson mixer set to approximately 2000 rpm in the Aqueous Phase the Organic phase was slowly poured into the Aqueous Phase. While slowly pouring the Organic phase the speed of the Silverson mix can slowly may be increased to approximately 4500 rpm as the last of the organic phase was added. The combined phases were mixed at 4500 rpm until the desired particle size was obtained. In this case the desired particle size was 10 microns. The Silverson mixer was stopped at the end of 90 seconds and the particle size checked. If the size was too large, the Silverson mixer was used at 4500 rpm for 10-15 second intervals until the desired particle size was obtained.

Fixation of the Capsule Walls

Once the desired particle size was obtained, the Silverson mixer was replaced with a low shear propeller style mixer. 2.32 grams of Ethylene Diamine was diluted in 20.84 grams of water to make a 10% EDA/water solution. The low shear mixer was started and all of the 10% EDA/Water mixture was slowly added dropwise. The batch was allowed to mix for an additional 15 minutes to complete the reaction.

Finishing the Batch

Maintaining the low shear agitation was maintained and the remaining 375.3 grams of water was added. The final batch was allowed to mix an additional 15 minutes then transferred to clean bottles.

This procedure can be used to make similar formulations. The wall thickness can be adjusted by increasing or decreasing the amount of PAPI® 27 and the amount of EDA. A corresponding quantity of water is used to offset the increases or decreases in the amounts of these components. The particle size can be adjusted by increasing or decreasing the intensity and time of shear mixing during the formation of the emulsion.

The following is an example of modifying the above protocol for the formation of 10/100 capsules. In this formulation, the particle size is the same 10 microns as the above but the wall thickness is adjusted from 40 nanometers to 100 nanometers. Increasing the wall thickness required increasing the PAPI® 27 in the Organic phase to 23.98 grams (18.18% of the composition) and the EDA was increased to 5.75 grams (4.37% of the composition). A corresponding quantity of water was removed to offset the PAPI® 27 and EDA increases. The aqueous phase and all of the processing steps remained the same as the 10/40 example.

Example 2

Volatility Testing

A series of capsules containing an oil phase of 11.66 wt % dithiopyr and possessing varying design of particle size/wall thickness were prepared. Specifically, capsules of 6/20, 10/10, 10/40, 10/70, and 10/100 design (expressed as X/Y where diameter in micrometers=X, and a wall thickness in nanometers=Y) were prepared and finished to contain a nominal level of 11.8 wt % dithiopyr. Methylated seed oil (MSO) or methyl salicylate (MeSal) was added during the formation of some formulations of 10/40 capsules so as to achieve a 3:1 ratio of dithiopyr to methyl salicylate or a ratio of 3:1 of dithiopyr to methylated seed oil. The finished formulations were diluted to 0.24% dithiopyr for the volatility test. 0.25 mL of the diluted samples and a control (Dimension 2EW (available from Dow)) were introduced onto 1 g sea sand in a 20 mL glass vial. The vials were placed uncapped in a 54° C. oven for 0, 3, and 7 days. Three repetitions for each time point were collected, extracted, and assayed for dithiopyr content. The results are presented in FIG. 1. Stand-alone capsules were identified that displayed a relatively linear decrease in dithiopyr content over the course of 59 days.

Example 3

Field Crabgrass Pre-Emergence Trials

Compositions comprising 11.8 wt % dithiopyr were tested on plots for their ability to control the growth of crabgrass (DIGSS (*Digitaria* sp.)) when applied prior to the emergence of the crabgrass. The compositions had 10/40 (GF2825), 10/100 (GF2826), or 10/40 mixed with methyl salicylate (GF2827) (expressed as X/Y where diameter in micrometers=X, and a wall thickness in nanometers=Y) capsules. Doses of 0.38 and 0.5 lbs active ingredient/acre dithiopyr were tested.

Figure 2:
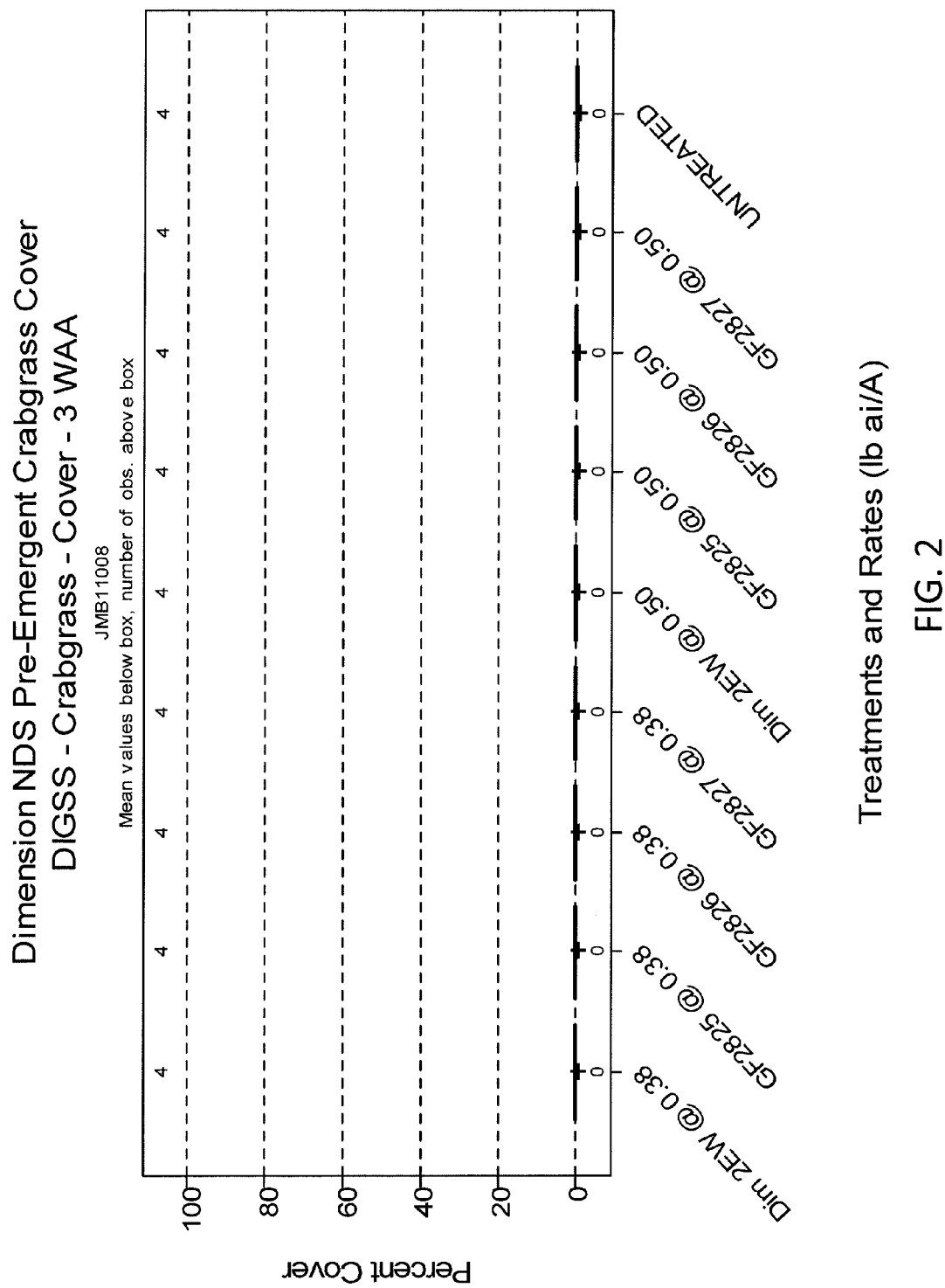
FIG. 2 is a graphical representation of the effects of pre-emergent application of various capsule sizes and diameters on crabgrass infestation noted as cover 3 Weeks After Application (WAA). Dim 2EW represents Dimension 2EW available from Dow. GF 2825 indicates 10/40 capsules. GF 2826 indicates 10/100 capsules. GF 2827 indicates 10/40 capsules with methyl salicylate.
Figure 3:
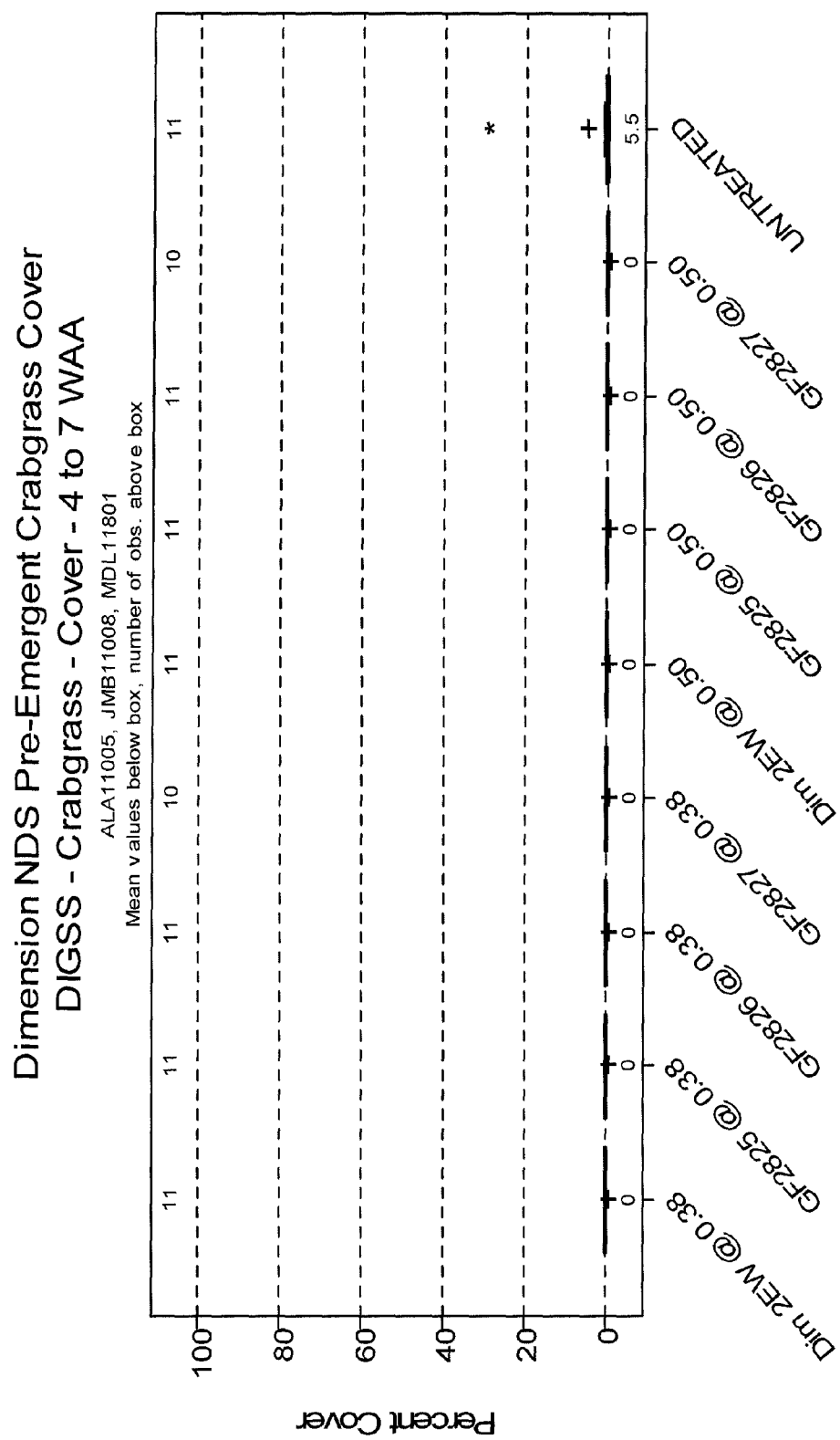
FIG. 3 is a graphical representation of the effects of pre-emergent application of various capsule sizes and diameters on crabgrass infestation noted as cover 4-7 Weeks After Application (WAA). Dim 2EW represents Dimension 2EW available from Dow. GF 2825 indicates 10/40 capsules. GF 2826 indicates 10/100 capsules. GF 2827 indicates 10/40 capsules with methyl salicylate.
Figure 4:
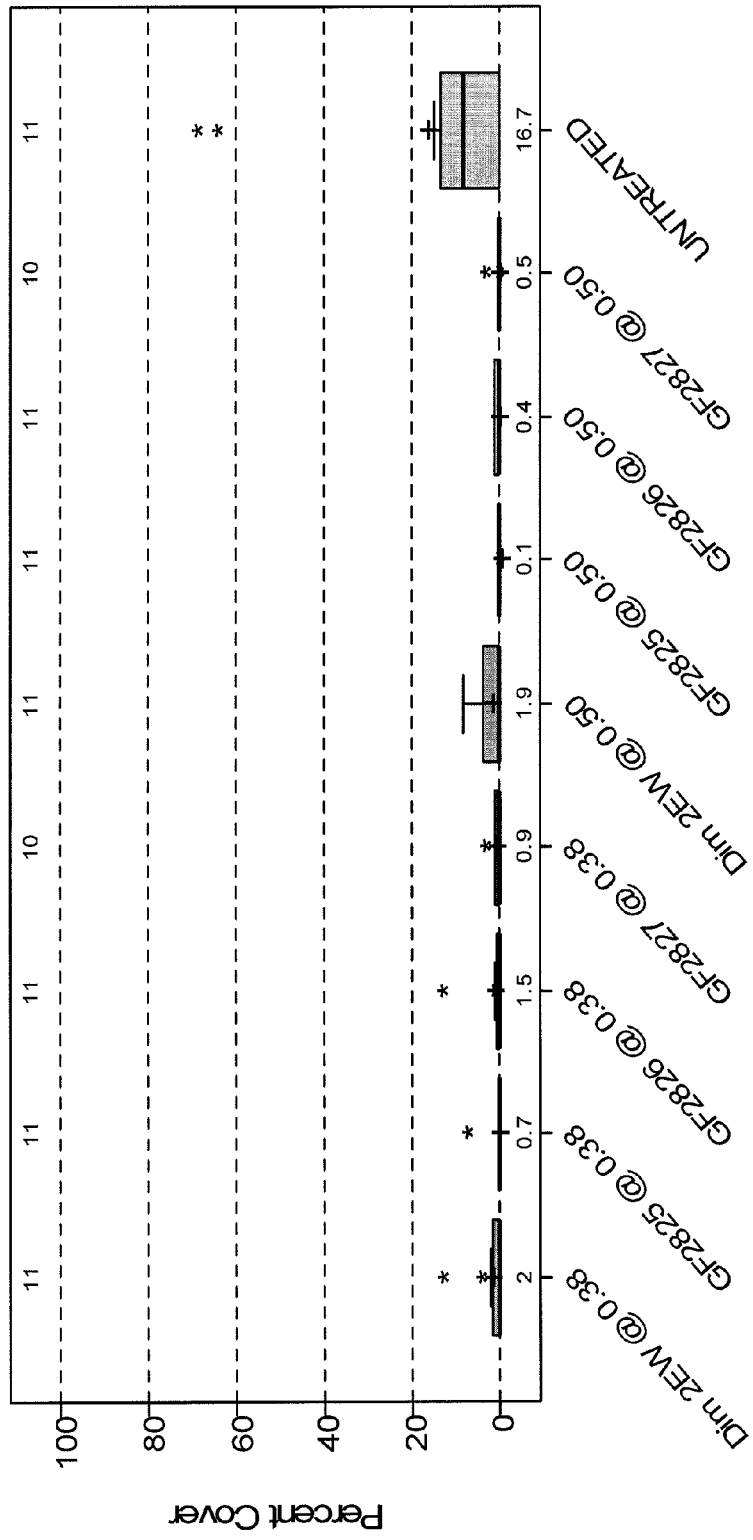
FIG. 4 is a graphical representation of the effects of pre-emergent application of various capsule sizes and diameters on crabgrass infestation noted as cover 8-11 Weeks After Application (WAA). Dim 2EW represents Dimension 2EW available from Dow. GF 2825 indicates 10/40 capsules. GF 2826 indicates 10/100 capsules. GF 2827 indicates 10/40 capsules with methyl salicylate.
Figure 5:
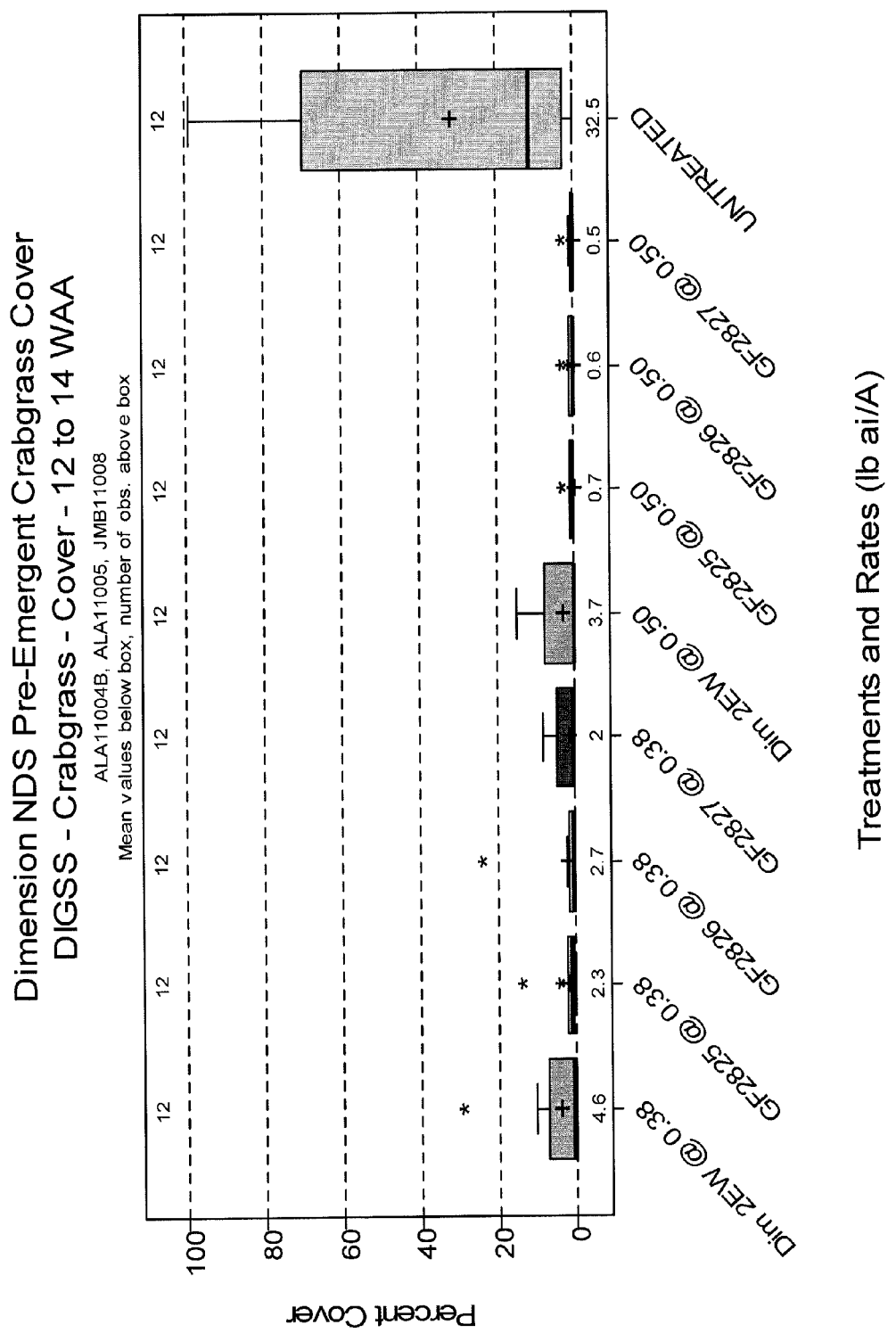
FIG. 5 is a graphical representation of the effects of pre-emergent application of various capsule sizes and diameters on crabgrass infestation noted as cover 12-14 Weeks After Application (WAA). Dim 2EW represents Dimension 2EW available from Dow. GF 2825 indicates 10/40 capsules. GF 2826 indicates 10/100 capsules. GF 2827 indicates 10/40 capsules with methyl salicylate.
Figure 6:
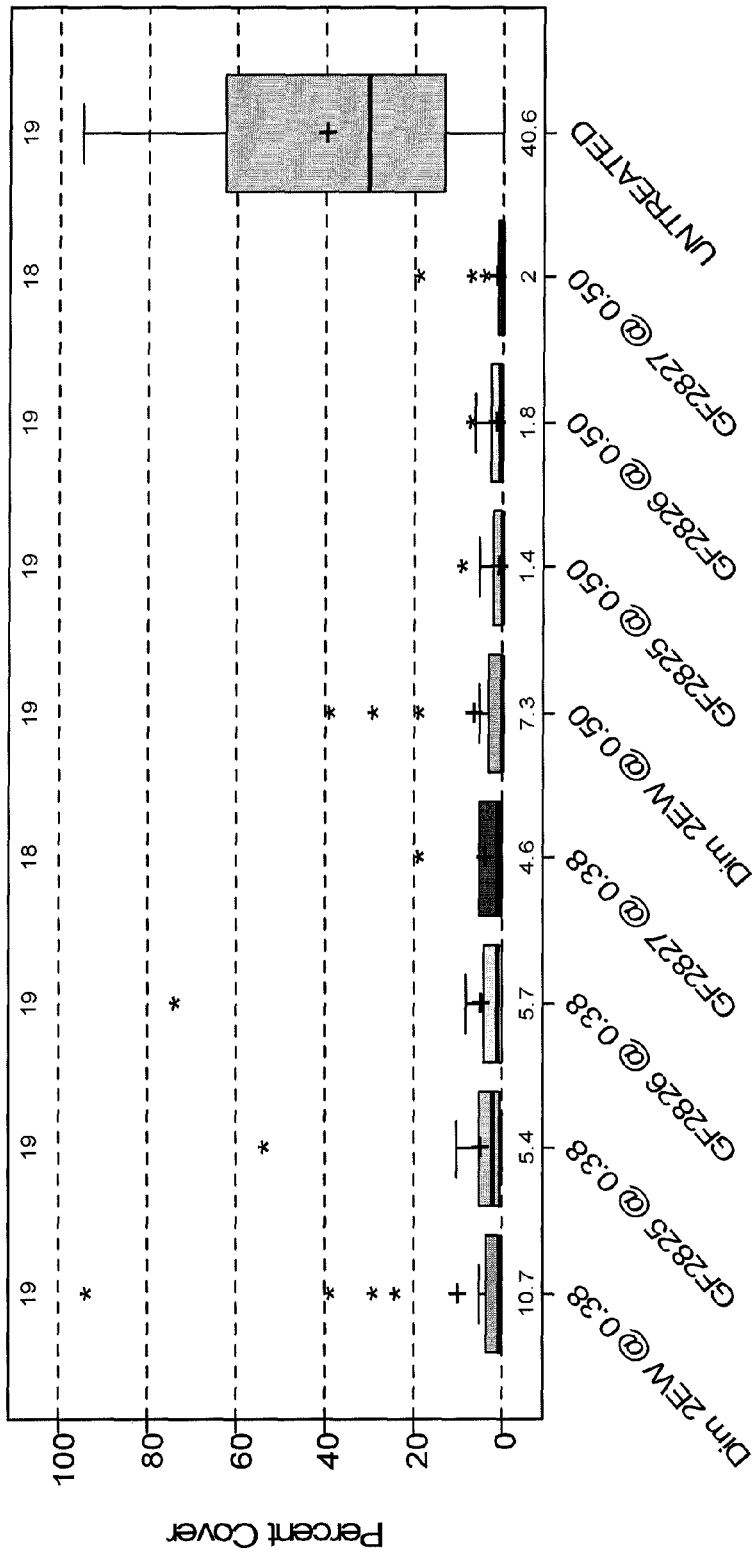
FIG. 6 is a graphical representation of the effects of pre-emergent application of various capsule sizes and diameters on crabgrass infestation noted as cover 16-18 Weeks After Application (WAA). Dim 2EW represents Dimension 2EW available from Dow. GF 2825 indicates 10/40 capsules. GF 2826 indicates 10/100 capsules. GF 2827 indicates 10/40 capsules with methyl salicylate.
Figure 7:
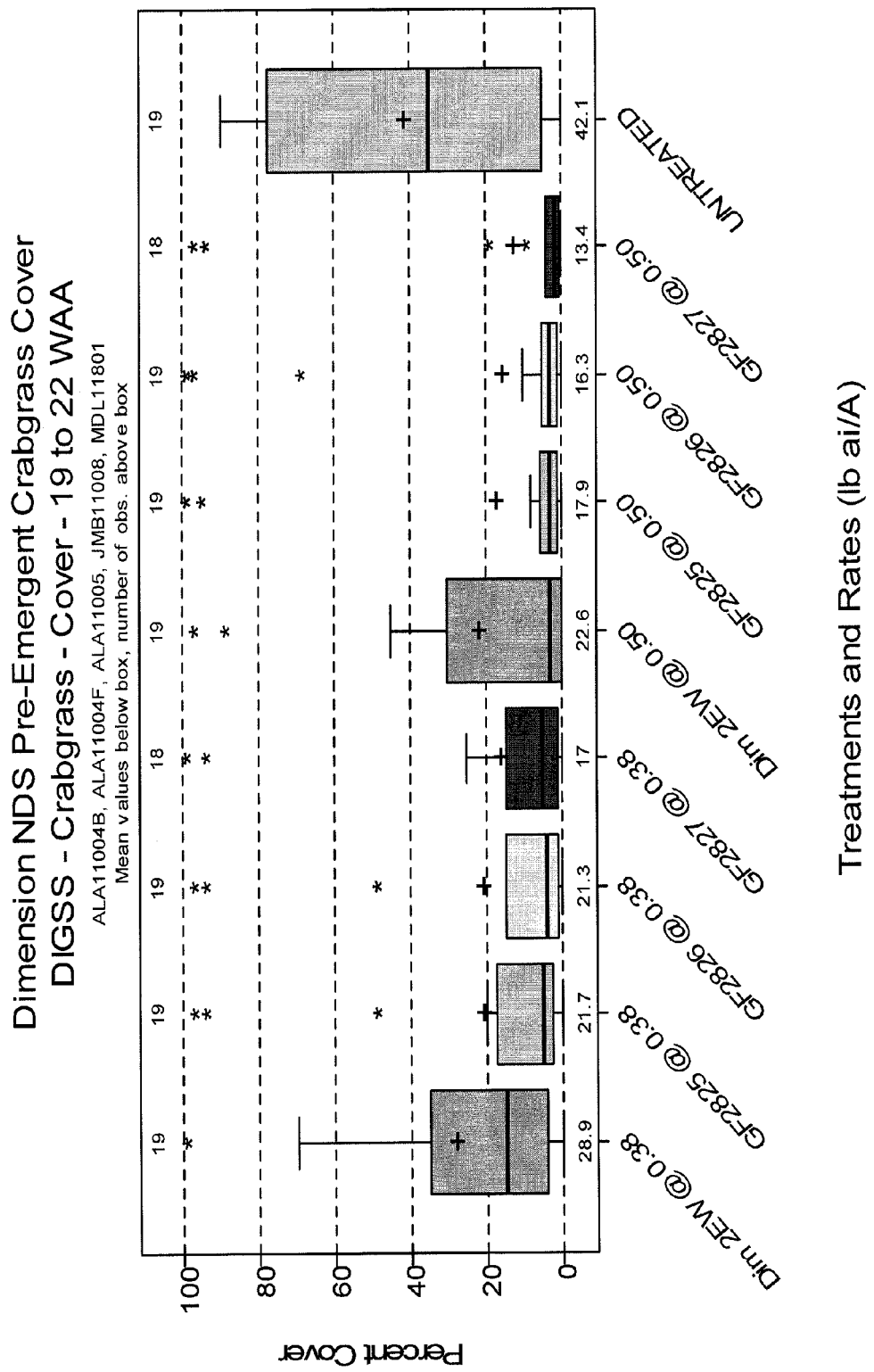
FIG. 7 is a graphical representation of the effects of pre-emergent application of various capsule sizes and diameters on crabgrass infestation noted as cover 19-22 Weeks After Application (WAA). Dim 2EW represents Dimension 2EW available from Dow. GF 2825 indicates 10/40 capsules. GF 2826 indicates 10/100 capsules. GF 2827 indicates 10/40 capsules with methyl salicylate.
Figure 8:
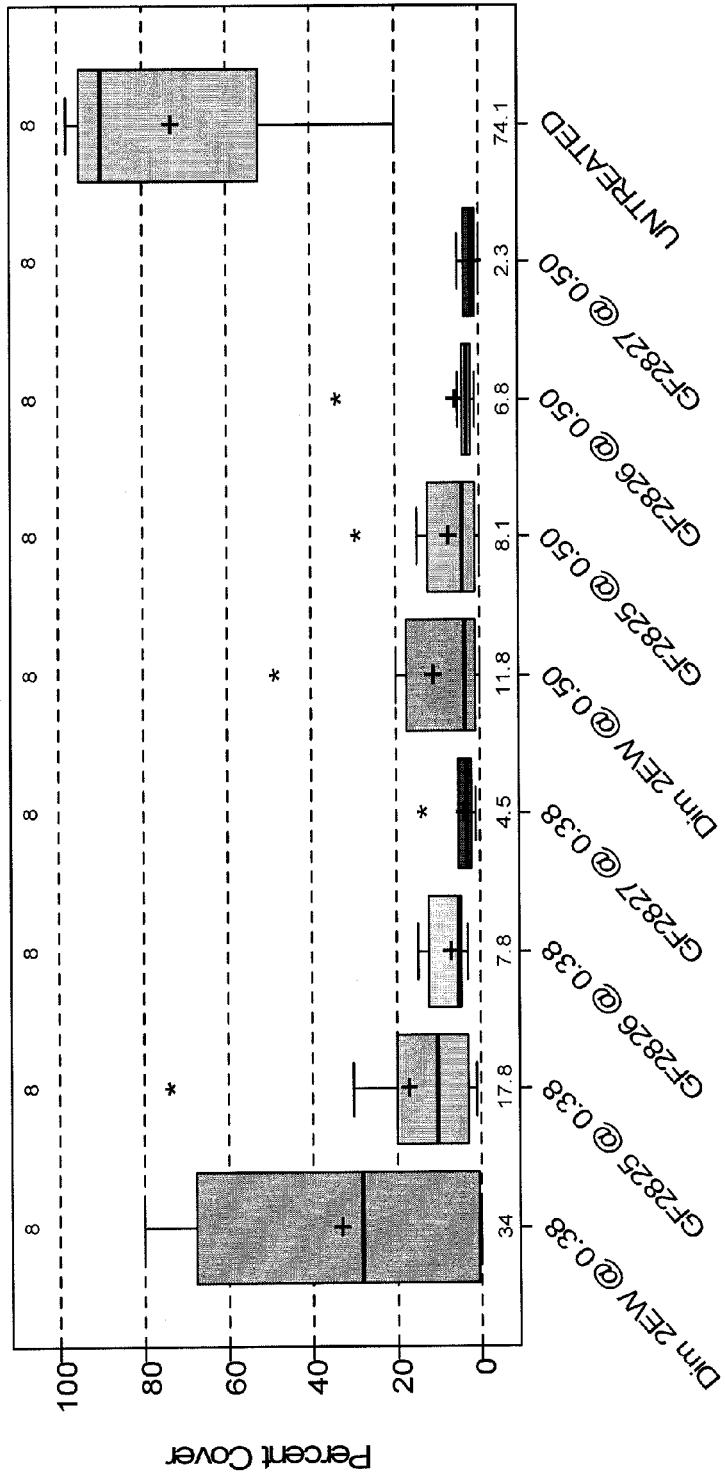
FIG. 8 is a graphical representation of the effects of pre-emergent application of various capsule sizes and diameters on crabgrass infestation noted as cover 24-27 Weeks After Application (WAA). Dim 2EW represents Dimension 2EW available from Dow. GF 2825 indicates 10/40 capsules. GF 2826 indicates 10/100 capsules. GF 2827 indicates 10/40 capsules with methyl salicylate.

FIG. 2 is a graphical representation of the effects of various capsule formulations applied pre-emergent 3 Weeks After Application (WAA) on the percentage of the plot covered by crabgrass. FIG. 3 is a graphical representation of the results of various capsule formulations applied pre-emergent 4-7 WAA on the percentage of the plot covered by crabgrass. FIG. 4 is a graphical representation of the results of various capsule formulations applied pre-emergent 8-11 WAA on the percentage of the plot covered by crabgrass. FIG. 5 is a graphical representation of the results of various capsule formulations applied pre-emergent 12-14 WAA on the percentage of the plot covered by crabgrass. FIG. 6 is a graphical representation of the results of various capsule formulations applied pre-emergent 16-18 WAA on the percentage of the plot covered by crabgrass. FIG. 7 is a graphical representation of the results of various capsule formulations applied pre-emergent 19-22 WAA on the percentage of the plot covered by crabgrass. FIG. 8 is a graphical representation of the results of various capsule formulations applied pre-emergent 24-27 WAA on the percentage of the plot covered by crabgrass.

Example 4

Field Crabgrass Pre-Emergence Trials

Compositions comprising 11.8 wt % dithiopyr were tested on plots for their ability to control the growth of crabgrass (DIGSS (*Digitaria* sp.)) when applied prior to the emergence of the crabgrass. The compositions had 10/40 (GF2825), 10/100 (GF2826), 10/40 mixed with methyl salicylate (GF2827), or a 1:1 mixture of 6/20 and 10/10 (GF2653) (expressed as X/Y where diameter in micrometers=X, and a wall thickness in nanometers=Y) capsules. Doses of 0.25, 0.38 and 0.5 lbs active ingredient/ acre dithiopyr were tested and compared to doses of 0.38, 0.5, and 0.67 lbs/acre, respectively, of Dimension 2EW (available from Dow).

Figure 9:
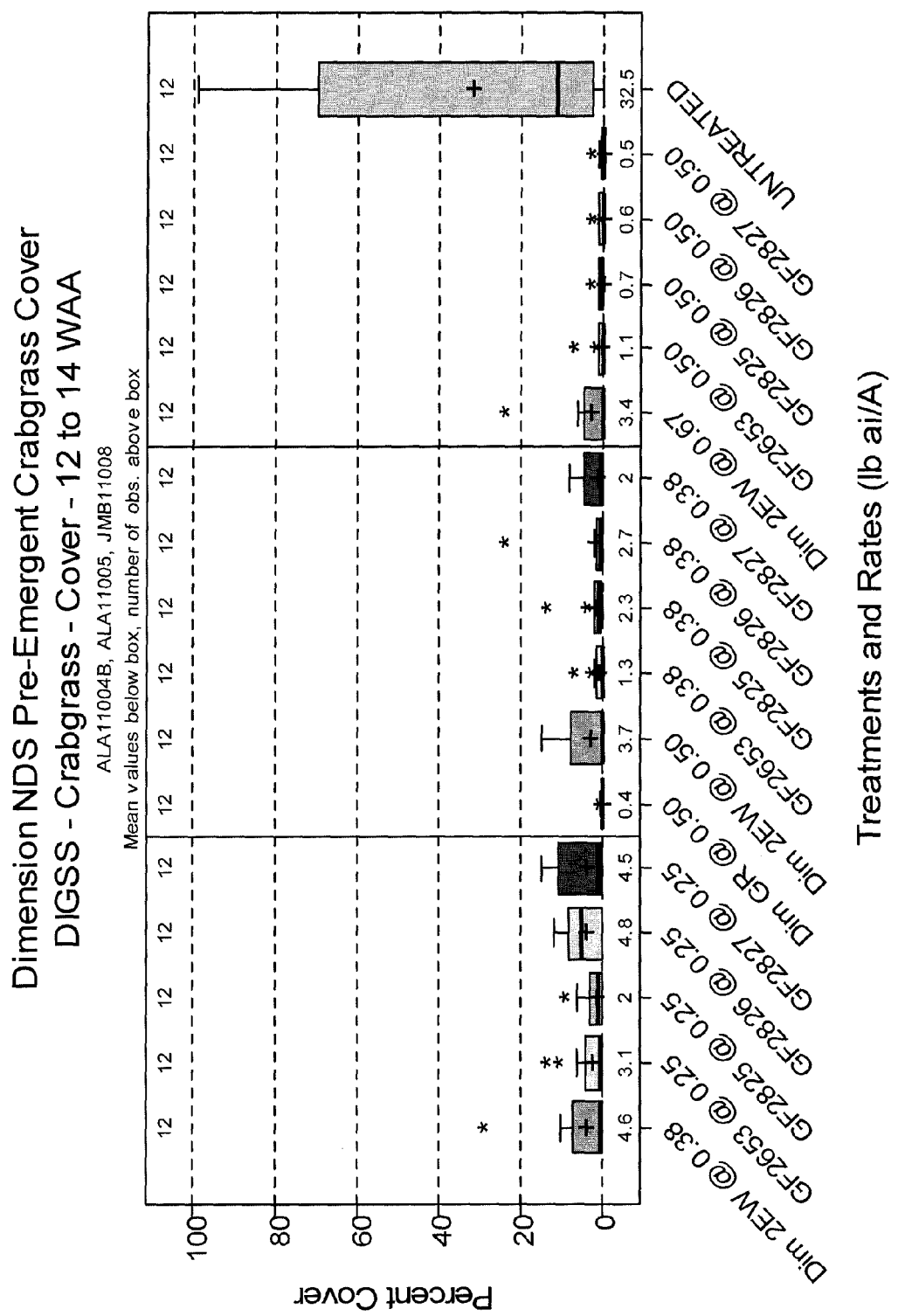
FIG. 9 is a graphical representation of the effects of pre-emergent application of various capsule sizes and diameters on crabgrass infestation noted as cover 12-14 Weeks After Application (WAA). Dim 2EW represents Dimension 2EW available from Dow. GF 2825 indicates 10/40 capsules. GF 2826 indicates 10/100 capsules. GF 2827 indicates 10/40 capsules with methyl salicylate. GF 2653 indicates a 1:1 mixture of 6/20 and 10/10 capsules.
Figure 10:
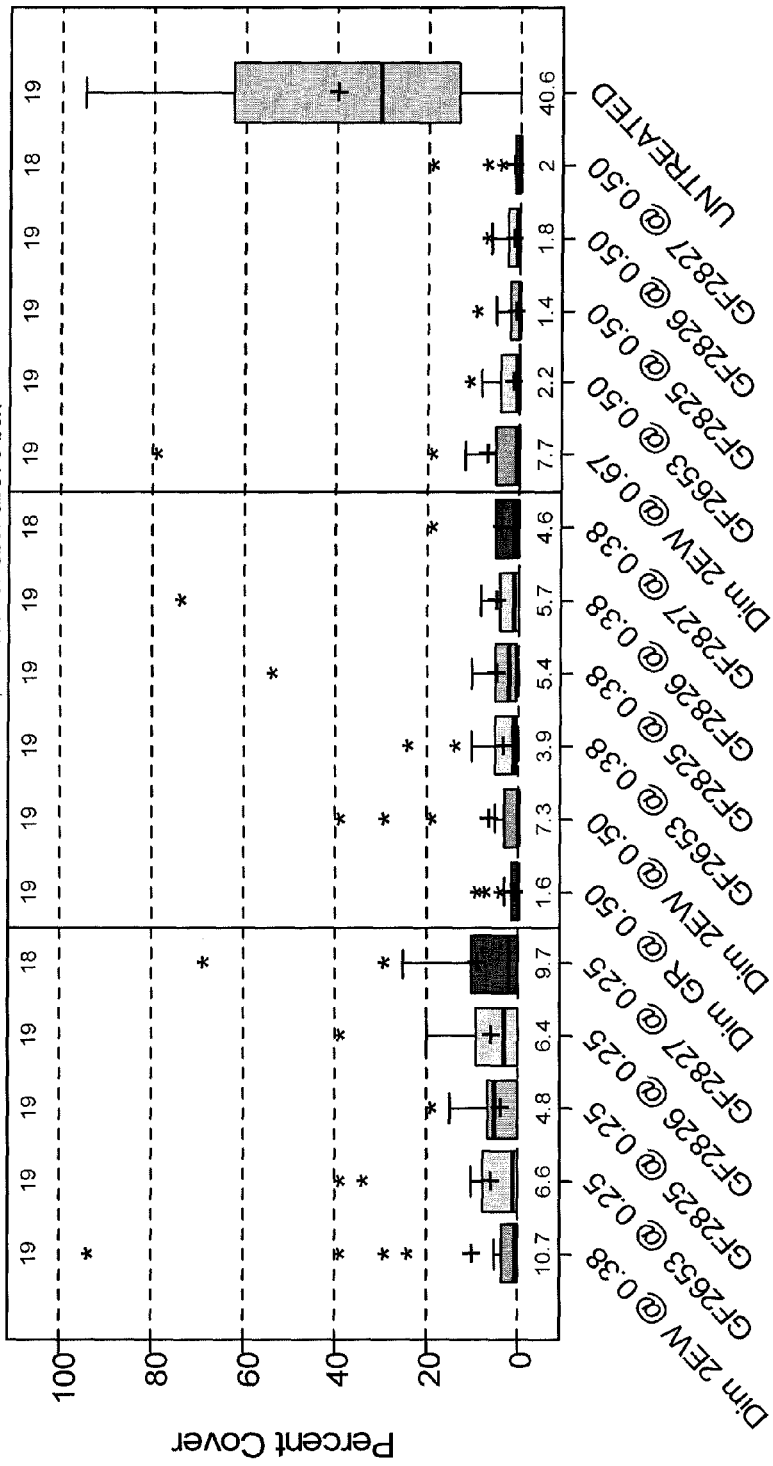
FIG. 10 is a graphical representation of the effects of pre-emergent application of various capsule sizes and diameters on crabgrass infestation noted as cover 16-18 Weeks After Application (WAA). Dim 2EW represents Dimension 2EW available from Dow. GF 2825 indicates 10/40 capsules. GF 2826 indicates 10/100 capsules. GF 2827 indicates 10/40 capsules with methyl salicylate. GF 2653 indicates a 1:1 mixture of 6/20 and 10/10 capsules.
Figure 11:
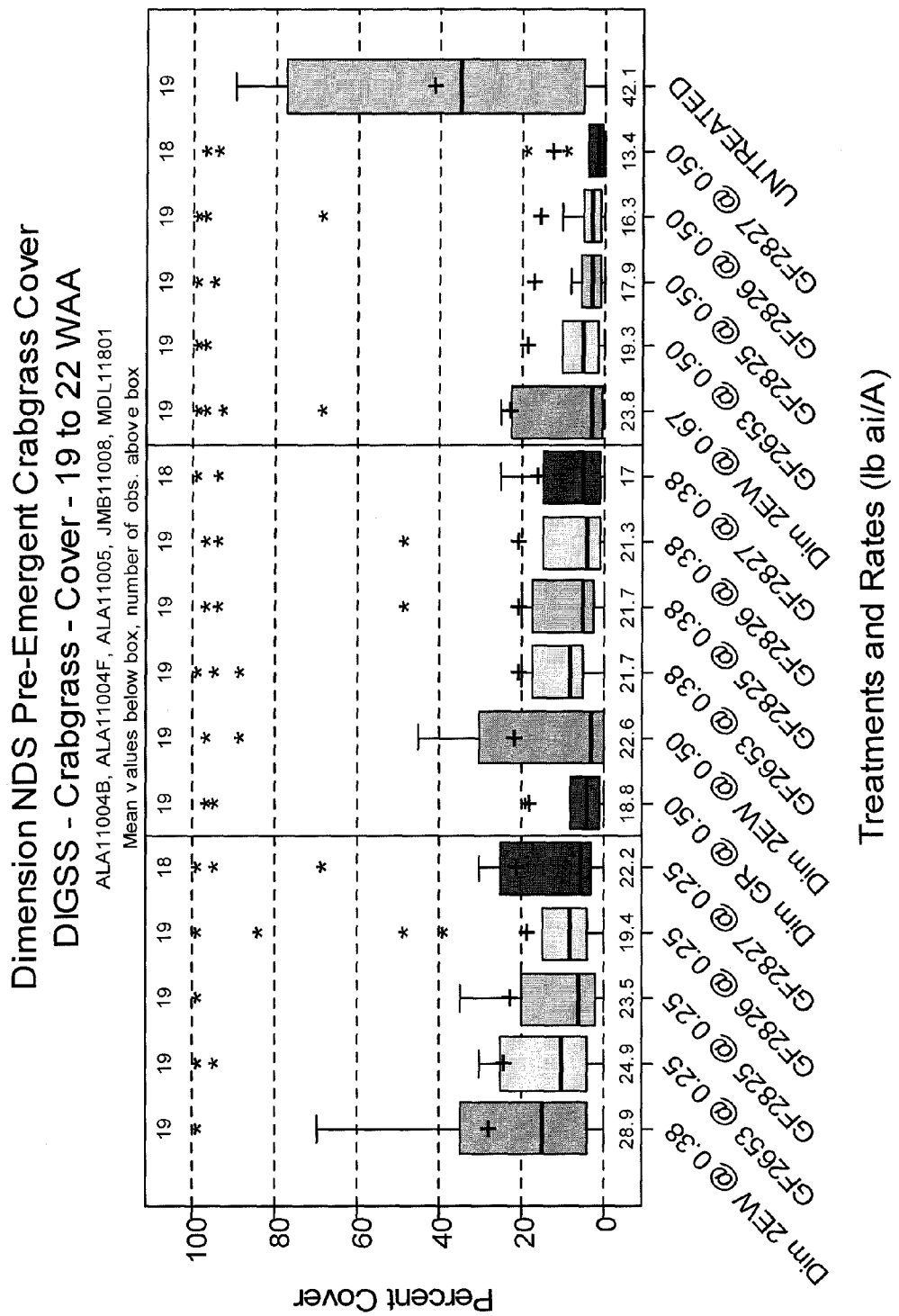
FIG. 11 is a graphical representation of the effects of pre-emergent application of various capsule sizes and diameters on crabgrass infestation noted as cover 19-22 Weeks After Application (WAA). Dim 2EW represents Dimension 2EW available from Dow. GF 2825 indicates 10/40 capsules. GF 2826 indicates 10/100 capsules. GF 2827 indicates 10/40 capsules with methyl salicylate. GF 2653 indicates a 1:1 mixture of 6/20 and 10/10 capsules.
Figure 12:
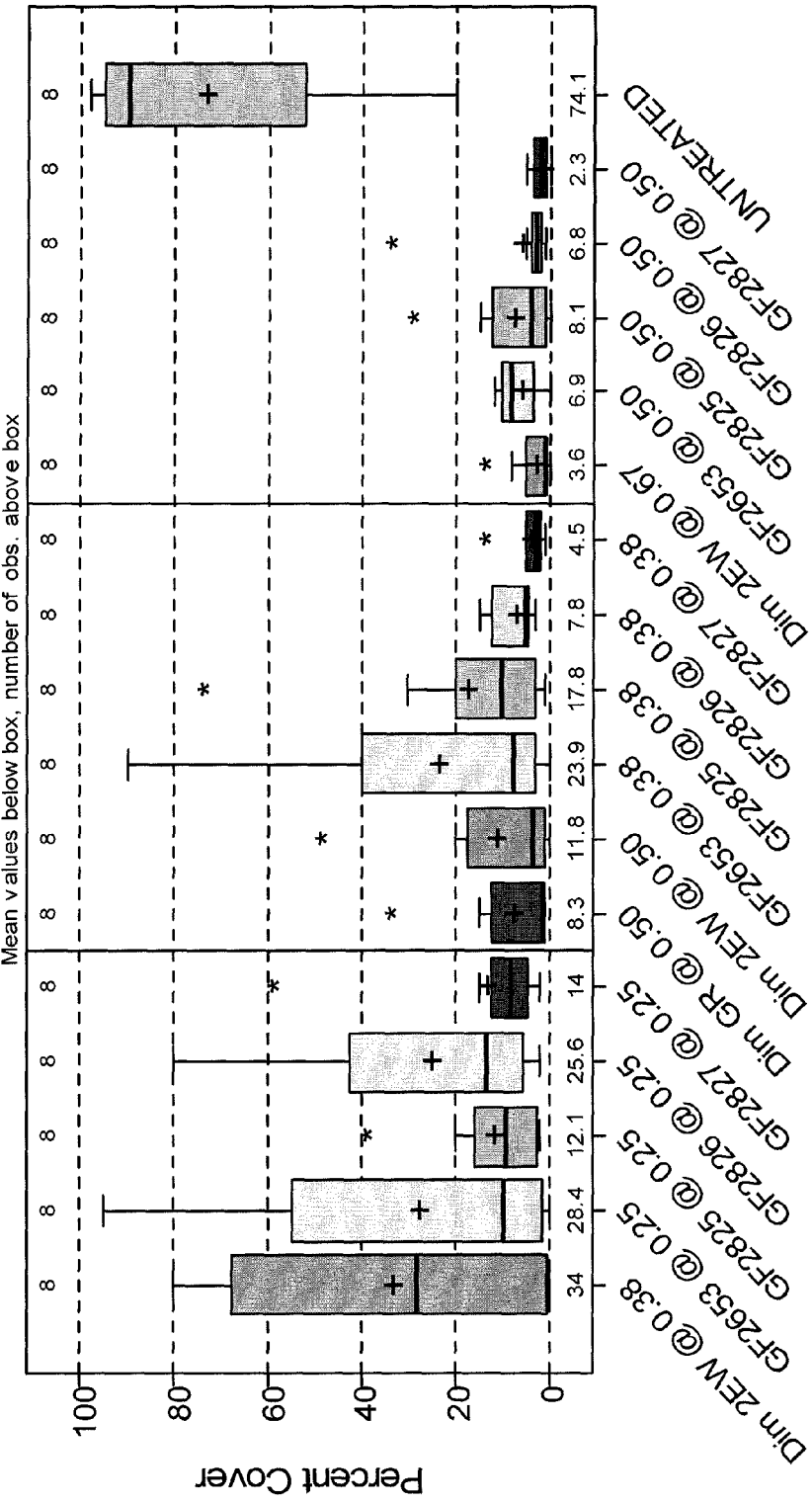
FIG. 12 is a graphical representation of the effects of pre-emergent application of various capsule sizes and diameters on crabgrass infestation noted as cover 24-27 Weeks After Application (WAA). Dim 2EW represents Dimension 2EW available from Dow. GF 2825 indicates 10/40 capsules. GF 2826 indicates 10/100 capsules. GF 2827 indicates 10/40 capsules with methyl salicylate. GF 2653 indicates a 1:1 mixture of 6/20 and 10/10 capsules.

FIG. 9 is a graphical representation of the effects of various capsule formulations applied pre-emergent 12-14 Weeks After Application (WAA) on the percentage of the plot covered by crabgrass. FIG. 10 is a graphical representation of the results of various capsule formulations applied pre-emergent 16-18 WAA on the percentage of the plot covered by crabgrass. FIG. 11 is a graphical representation of the results of various capsule formulations applied pre-emergent 19-22 WAA on the percentage of the plot covered by crabgrass. FIG. 12 is a graphical representation of the results of various capsule formulations applied pre-emergent 24-27 WAA on the percentage of the plot covered by crabgrass.

Example 5

Field Crabgrass Post-Emergence Trials

Compositions comprising 11.8 wt % dithiopyr were tested on plots for their ability to control the growth of crabgrass (DIGIS (*Digitaria ischaemum*)) when applied to the crabgrass post emergent at the 1-2 leaf stage. The compositions had 10/40 (GF2825), 10/100 (GF2826) (expressed as X/Y where diameter in micrometers=X, and a wall thickness in nanometers=Y) capsules. Doses of 0.25, 0.38 and 0.5 lbs active ingredient/acre dithiopyr were tested and compared to untreated plots.

Figure 13:
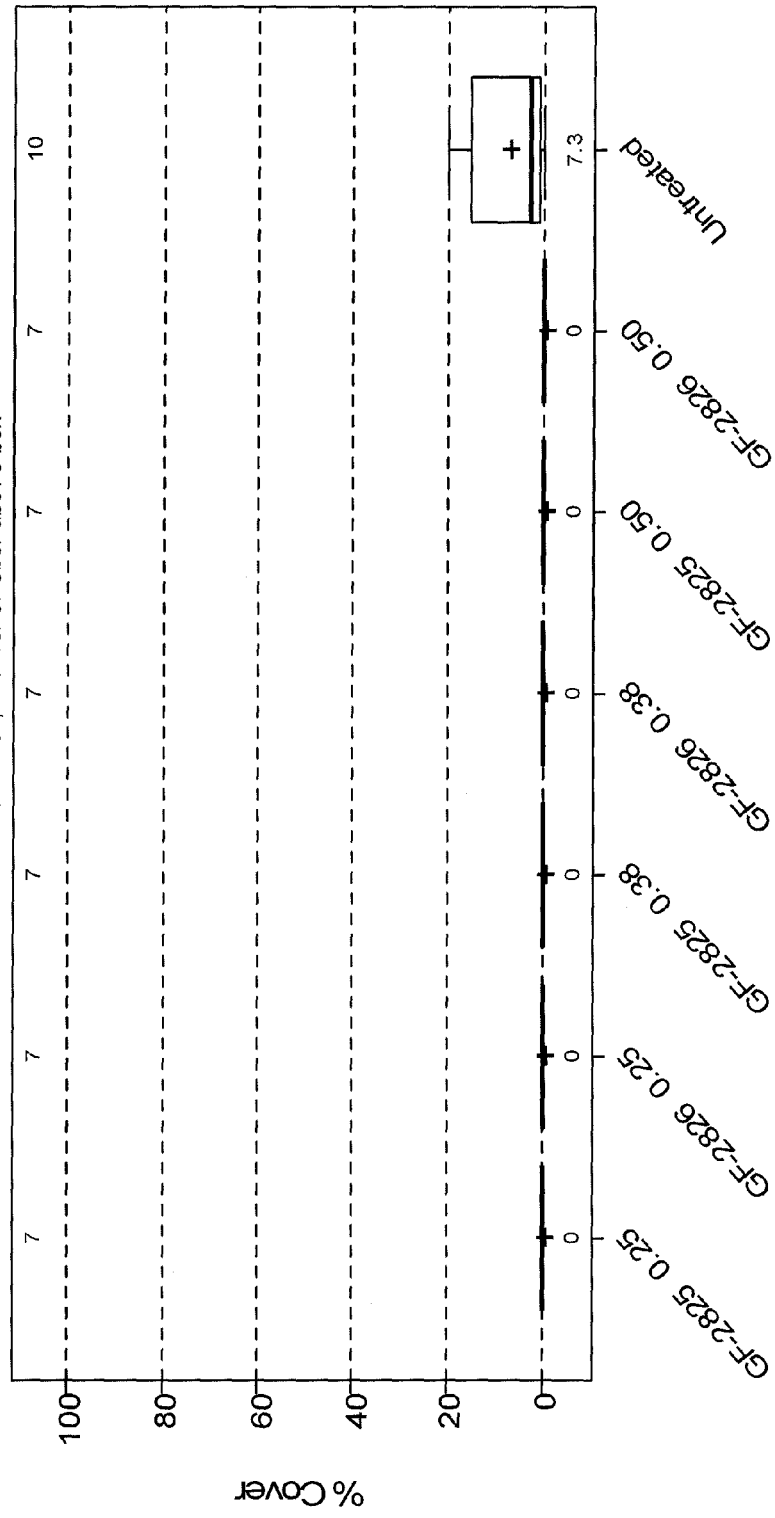
FIG. 13 is a graphical representation of the effects of post-emergent (1-2 leaf stage) application of various capsule sizes and diameters on crabgrass infestation noted as cover 3-5 Weeks After Application (WAA). GF 2825 indicates 10/40 capsules. GF 2826 indicates 10/100 capsules.
Figure 14:
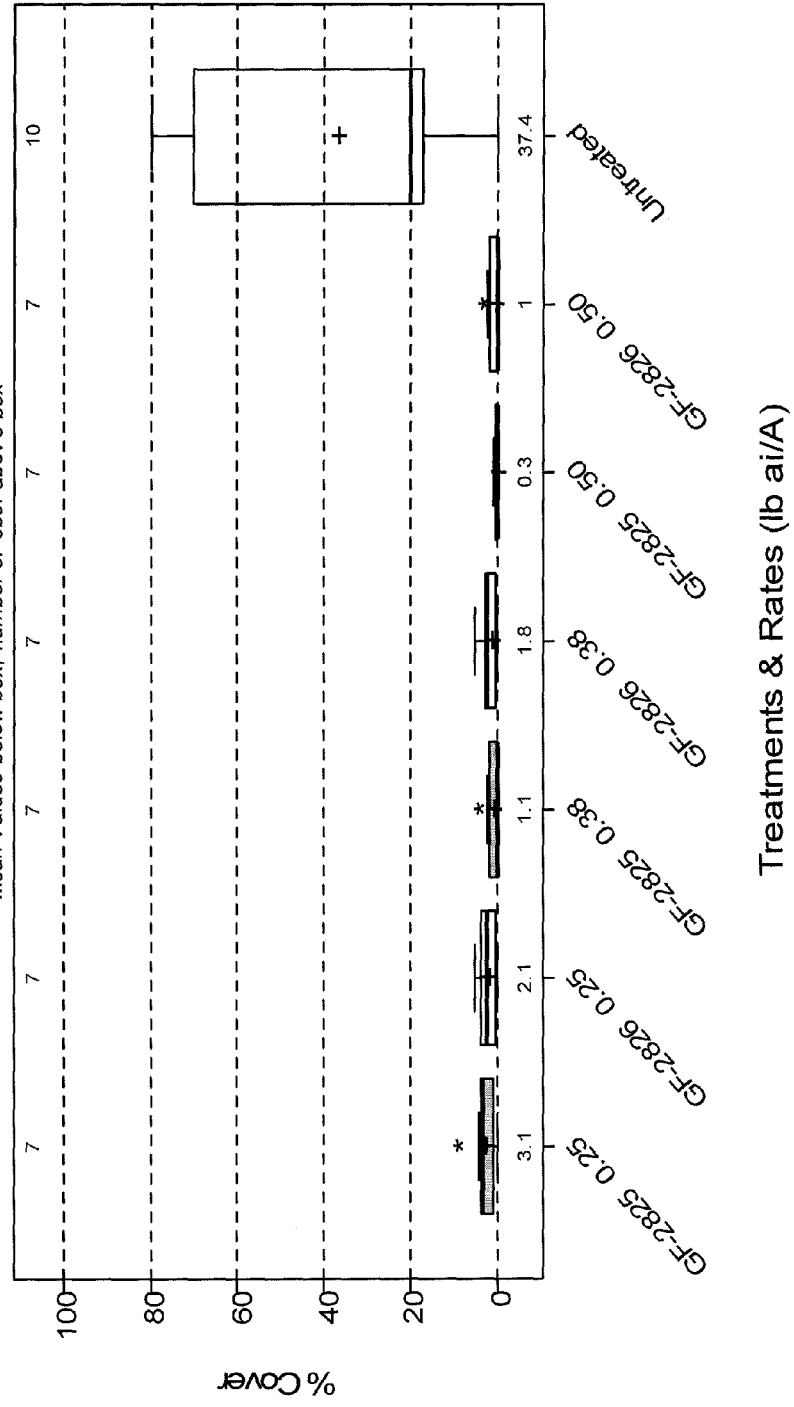
FIG. 14 is a graphical representation of the effects of post-emergent (1-2 leaf stage) application of various capsule sizes and diameters on crabgrass infestation noted as cover 6-10 Weeks After Application (WAA). GF 2825 indicates 10/40 capsules. GF 2826 indicates 10/100 capsules.
Figure 15:
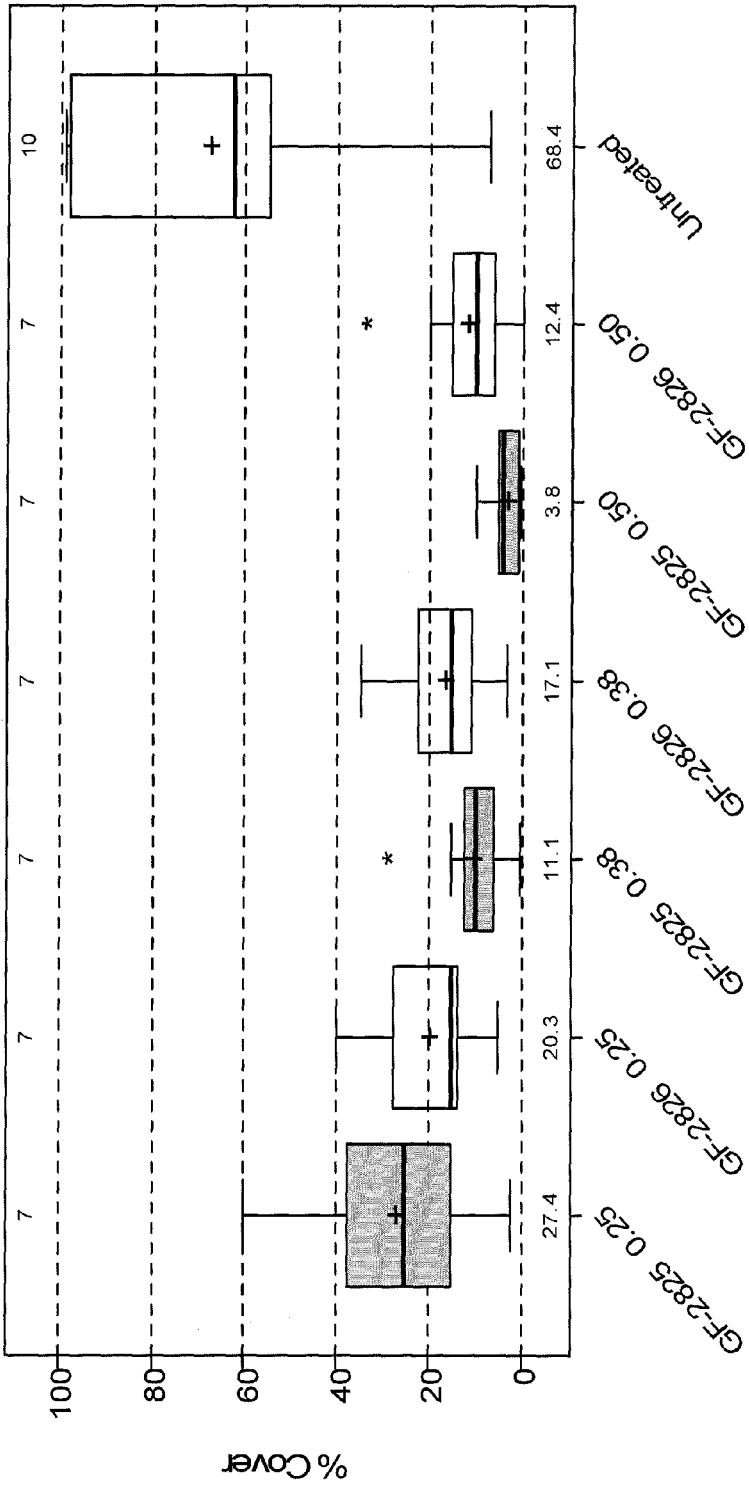
FIG. 15 is a graphical representation of the effects of post-emergent (1-2 leaf stage) application of various capsule sizes and diameters on crabgrass infestation noted as cover 11-14 Weeks After Application (WAA). GF 2825 indicates 10/40 capsules. GF 2826 indicates 10/100 capsules.
Figure 16:
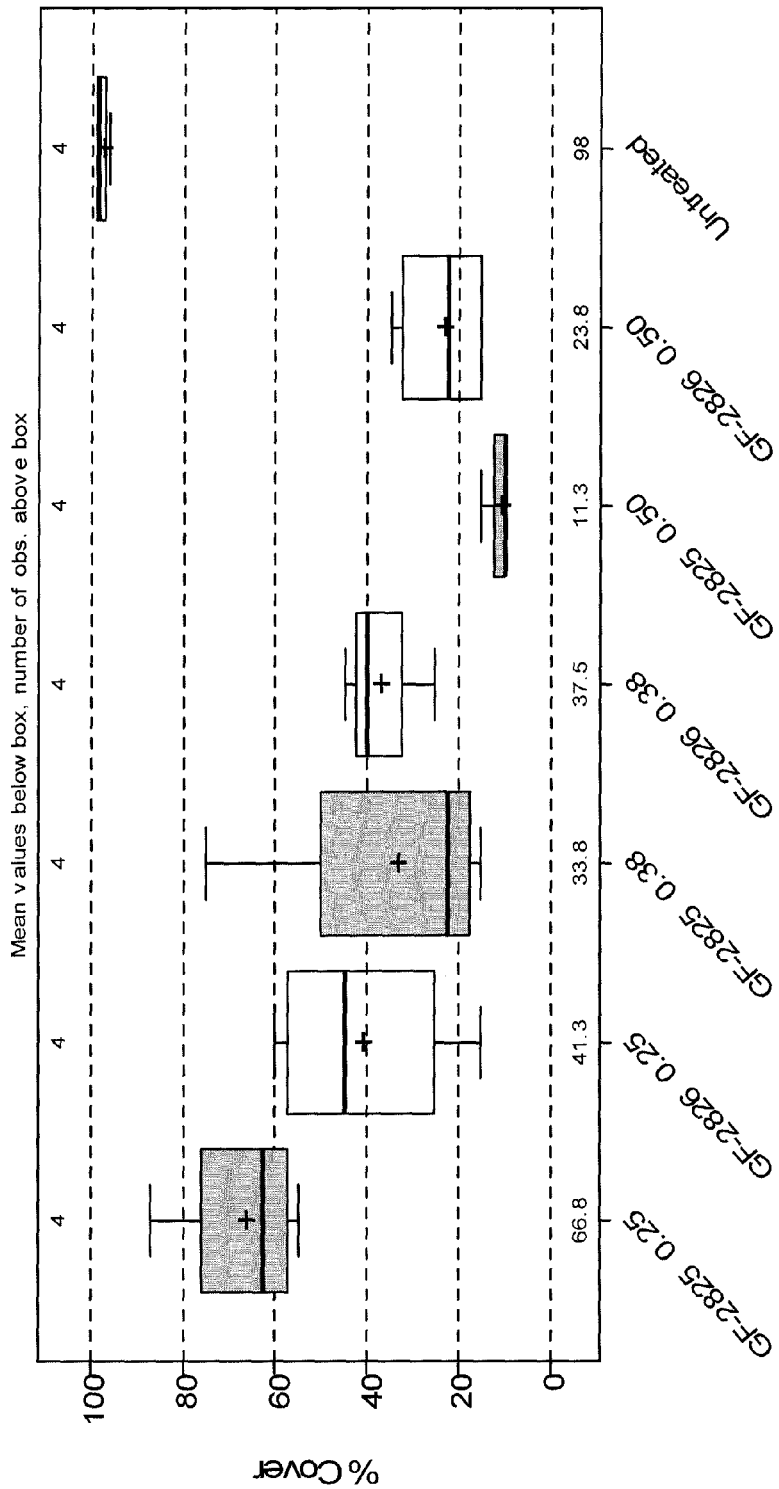
FIG. 16 is a graphical representation of the effects of post-emergent (1-2 leaf stage) application of various capsule sizes and diameters on crabgrass infestation noted as cover 15-17 Weeks After Application (WAA). GF 2825 indicates 10/40 capsules. GF 2826 indicates 10/100 capsules.

FIG. 13 is a graphical representation of the effects of various capsule formulations applied post-emergent 3-5 Weeks After Application (WAA) on the percentage of the plot covered by crabgrass. FIG. 14 is a graphical representation of the results of various capsule formulations applied post-emergent 6-10 WAA on the percentage of the plot covered by crabgrass. FIG. 15 is a graphical representation of the results of various capsule formulations applied post-emergent 11-14 WAA on the percentage of the plot covered by crabgrass. FIG. 15 is a graphical representation of the results of various capsule formulations applied post-emergent 15-17 WAA on the percentage of the plot covered by crabgrass.

Example 6

Field Crabgrass Post-Emergence Trials

Compositions comprising 11.8 wt % dithiopyr were tested on plots for their ability to control the growth of crabgrass (DIGIS (*Digitaria ischaemum*)) when applied to the crabgrass post emergent at the 1-2 leaf stage. The compositions had 10/40 (GF2825), 10/100 (GF2826), 10/40 mixed with methyl salicylate (GF2827), or a 1:1 mixture of 6/20 and 10/10 (GF2653) (expressed as X/Y where diameter in micrometers=X, and a wall thickness in nanometers=Y) capsules. Doses of 0.25, 0.38 and 0.5 lbs active ingredient/acre dithiopyr were tested and compared to untreated plots or plots treated with Dimension fertilizer or Dimension 2EW (both available from Dow) at doses of 0.25, 0.38 and 0.5 lbs active ingredient/acre dithiopyr.

Figure 17:
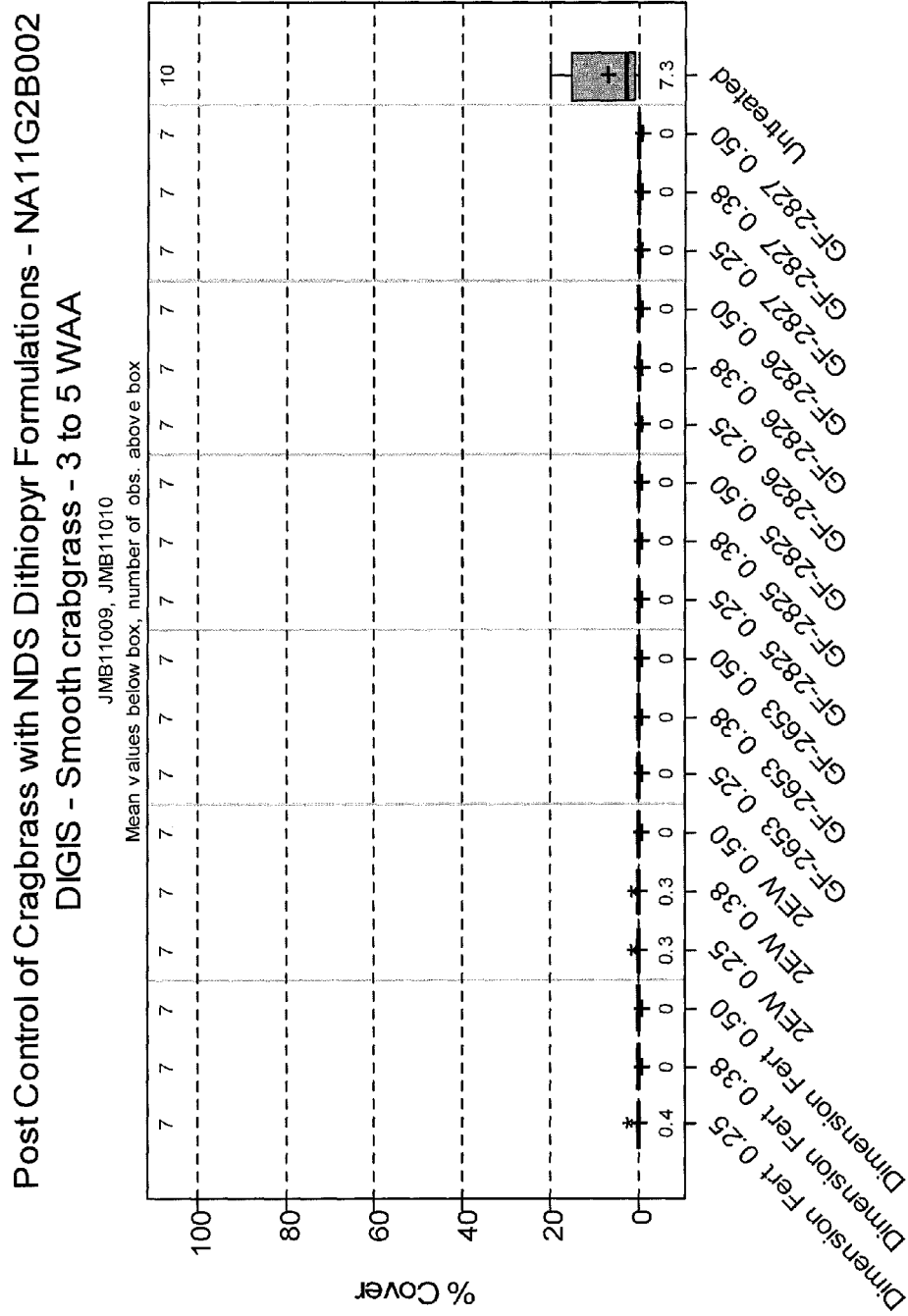
FIG. 17 is a graphical representation of the effects of post-emergent (1-2 leaf stage) application of various capsule sizes and diameters on crabgrass infestation noted as cover 3-5 Weeks After Application (WAA). GF 2825 indicates 10/40 capsules. Dimension Fert and 2EW represents Dimension on Fertilizer and Dimension 2EW respectively with both available from Dow. GF 2826 indicates 10/100 capsules. GF 2827 indicates 10/40 capsules with methyl salicylate. GF 2653 indicates a 1:1 mixture of 6/20 and 10/10 capsules.
Figure 18:
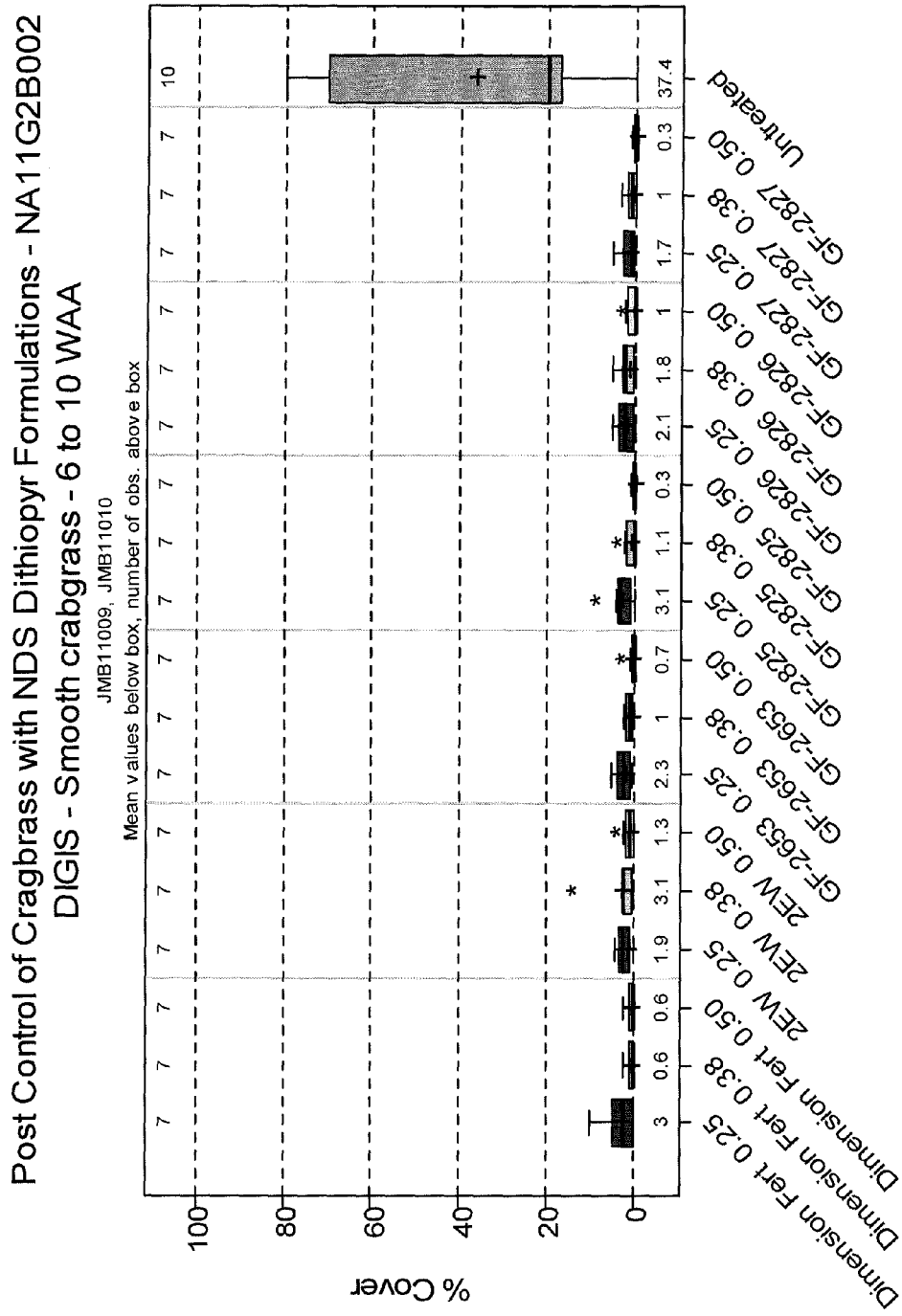
FIG. 18 is a graphical representation of the effects of post-emergent (1-2 leaf stage) application of various capsule sizes and diameters on crabgrass infestation noted as cover 6-10 Weeks After Application (WAA). GF 2825 indicates 10/40 capsules. Dimension Fert and 2EW represents Dimension on Fertilizer and Dimension 2EW respectively with both available from Dow. GF 2826 indicates 10/100 capsules. GF 2827 indicates 10/40 capsules with methyl salicylate. GF 2653 indicates a 1:1 mixture of 6/20 and 10/10 capsules.
Figure 19:
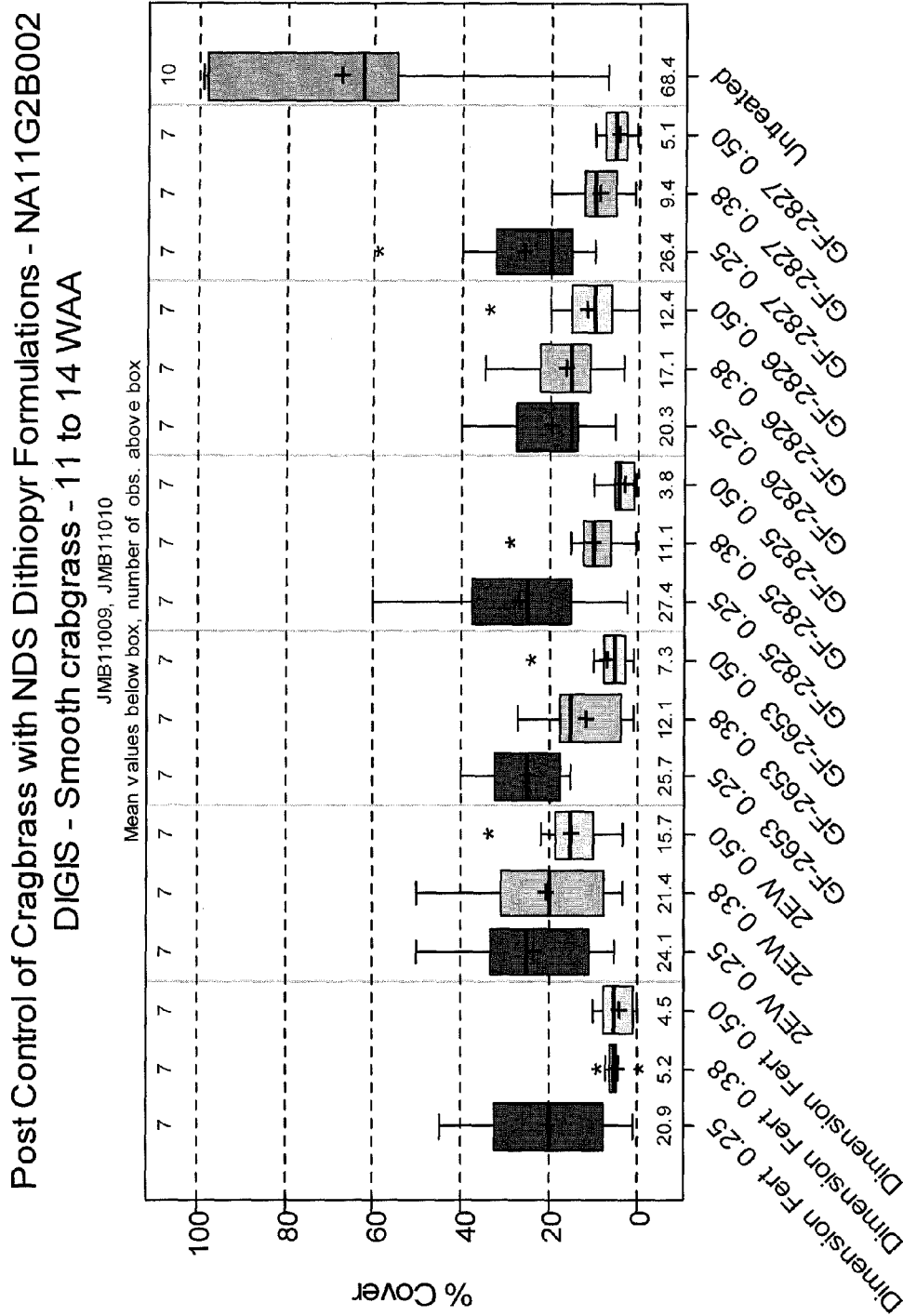
FIG. 19 is a graphical representation of the effects of post-emergent (1-2 leaf stage) application of various capsule sizes and diameters on crabgrass infestation noted as cover 11-14 Weeks After Application (WAA). Dimension Fert and 2EW represents Dimension on Fertilizer and Dimension 2EW respectively with both available from Dow. GF 2825 indicates 10/40 capsules. GF 2826 indicates 10/100 capsules. GF 2827 indicates 10/40 capsules with methyl salicylate. GF 2653 indicates a 1:1 mixture of 6/20 and 10/10 capsules.

FIG. 17 is a graphical representation of the effects of various capsule formulations applied post-emergent 3-5 Weeks After Application (WAA) on the percentage of the plot covered by crabgrass. FIG. 18 is a graphical representation of the results of various capsule formulations applied post-emergent 6-10 WAA on the percentage of the plot covered by crabgrass. FIG. 19 is a graphical representation of the results of various capsule formulations applied post-emergent 11-14 WAA on the percentage of the plot covered by crabgrass.

What is claimed is:

1. A composition comprising:
    first capsules having a diameter of about 10 micrometers and a wall thickness of about 10 nanometers; and
    second capsules having a diameter of from about 1 micrometer to about 10 micrometers and a wall thickness of from about 20 nanometers to about 100 nanometers,
    wherein the first and second capsules at least partially encapsulate dithiopyr, wherein the first capsules and the second capsules are different and the first capsules and the second capsules are present in the composition.
2. The composition of claim 1, wherein the second capsules have one or more diameters selected from the group consisting of 2, 6, and 10 micrometers.
3. The composition of claim 1, wherein the second capsules have a diameter of about 10 micrometers and a wall thickness of about 100 nanometers.
4. The composition of claim 1, wherein the second capsules have one or more wall thicknesses selected from the group consisting of 20, 30, 60, and 100 nanometers.
5. The composition of claim 1, wherein the dithiopyr is dispersed in an organic phase.
6. The composition of claim 1, wherein the second capsules have a diameter of about 10 micrometers and a wall thickness of about 70 nanometers.
7. The composition of claim 1, wherein the first and second capsules each comprises a polymeric composition.
8. The composition of claim 7, wherein the polymeric composition is a polyurea.
9. The composition of claim 1 comprising from about 120 to about 240 g/L dithiopyr.
10. The composition of claim 1 comprising about 12 wt % dithiopyr.
11. The composition of claim 1, wherein the composition further comprises methyl salicylate.
12. The composition of claim 11, wherein the dithiopyr:methyl salicylate is present at about a ratio of 3:1 of dithiopyr:methyl salicylate.
13. A composition comprising:
    first capsules having a diameter of about 10 micrometers and a wall thickness of about 10 nanometers; and
    second capsules having an average diameter of about 6 micrometers and having an average wall thickness of about 20 nanometers,
    wherein the first and second capsules at least partially encapsulate dithiopyr, wherein the first capsules and the second capsules are different and the first capsules and the second capsules are present in the composition.
14. The composition of claim 13, further comprising methyl salicylate.
15. The composition of claim 14, wherein the dithiopyr:methyl salicylate is present at about a ratio of 3:1 of dithiopyr:methyl salicylate.
16. The composition of claim 13, wherein the dithiopyr is dispersed in an organic phase.
17. The composition of claim 16, wherein the organic phase is hydrocarbon fluid.
18. The composition of claim 13, wherein the capsule comprises a polymeric composition.
19. The composition of claim 18, wherein the polymeric composition is a polyurea.

20. The composition of claim 13 comprising from about 120 to about 240g/L dithiopyr.

21. The composition of claim 13 comprising about 12 wt % dithiopyr.

22. A composition comprising capsules, wherein the capsules comprise about a 1:1 mixtures of first and second capsules which are different capsules present in the composition,
   wherein the first capsules having an average diameter of about 6 micrometers and an average wall thickness of about 20 nanometers;
   wherein the second capsules have an average diameter of about 10 micrometers and an average wall thickness of about 10 nanometers; and
   wherein the first and second capsules at least partially encapsulate dithiopyr.

23. The composition of claim 22, further comprising methyl salicylate.

24. The composition of claim 23, wherein the dithiopyr:methyl salicylate is present at about a ratio of 3:1 of dithiopyr:methyl salicylate.

25. The composition of claim 22, wherein the dithiopyr is dispersed in an organic phase.

26. The composition of claim 22, wherein the organic phase is hydrocarbon fluid.

27. The composition of claim 22, wherein the capsule comprises a polymeric composition.

28. The composition of claim 27, wherein the polymeric composition is a polyurea.

29. The composition of claim 22 comprising from about 120 to about 240 g/L dithiopyr.

30. The composition of claim 22 comprising about 12 wt % dithiopyr.

* * * * *